US012583919B2

(12) United States Patent
Sidhu et al.

(10) Patent No.: US 12,583,919 B2
(45) Date of Patent: Mar. 24, 2026

(54) ANTIBODIES THAT BIND TO LRP6 PROTEINS AND METHODS OF USE

(71) Applicant: ANTLERA THERAPEUTICS INC., Toronto (CA)

(72) Inventors: Sachdev S. Sidhu, Toronto (CA); Guohua Pan, Oakville (CA); Nish Patel, Scarborough (CA); Jason Moffat, Toronto (CA); Stephane Angers, Mississauga (CA); Jarrett Adams, Toronto (CA); Jagath R. Junutula, Fremont, CA (US)

(73) Assignee: ANTLERA THERAPEUTICS INC., Toronto (CA)

( * ) Notice: Subject to any disclaimer, the term of this patent is extended or adjusted under 35 U.S.C. 154(b) by 1005 days.

(21) Appl. No.: 17/634,916

(22) PCT Filed: Aug. 14, 2020

(86) PCT No.: PCT/CA2020/051120
§ 371 (c)(1),
(2) Date: Feb. 11, 2022

(87) PCT Pub. No.: WO2021/026666
PCT Pub. Date: Feb. 18, 2021

(65) Prior Publication Data
US 2022/0281969 A1 Sep. 8, 2022

Related U.S. Application Data

(60) Provisional application No. 62/886,918, filed on Aug. 14, 2019.

(51) Int. Cl.
| | |
|---|---|
| *C07K 16/28* | (2006.01) |
| *A61K 31/337* | (2006.01) |
| *A61K 31/404* | (2006.01) |
| *A61K 31/4745* | (2006.01) |
| *A61K 31/5517* | (2006.01) |
| *A61K 31/704* | (2006.01) |
| *A61K 38/07* | (2006.01) |
| *A61K 38/08* | (2019.01) |
| *A61K 38/15* | (2006.01) |
| *A61K 39/395* | (2006.01) |
| *A61P 35/00* | (2006.01) |
| *G01N 33/68* | (2006.01) |

(52) U.S. Cl.
CPC ............ *C07K 16/28* (2013.01); *A61K 31/337* (2013.01); *A61K 31/404* (2013.01); *A61K 31/4745* (2013.01); *A61K 31/5517* (2013.01); *A61K 31/704* (2013.01); *A61K 38/07* (2013.01); *A61K 38/08* (2013.01); *A61K 38/15* (2013.01); *A61K 39/3955* (2013.01); *A61P 35/00* (2018.01); *C07K 16/2863* (2013.01);

*G01N 33/6872* (2013.01); *C07K 2317/24* (2013.01); *C07K 2317/31* (2013.01); *C07K 2317/622* (2013.01)

(58) Field of Classification Search
CPC ................ C07K 16/28; C07K 16/2863; C07K 2317/24; C07K 2317/31; C07K 2317/622; C07K 2317/21; C07K 2317/33; C07K 2317/55; C07K 2317/75; C07K 2317/76; C07K 2317/92; C07K 2317/565; A61K 31/337; A61K 31/352; A61K 31/404; A61K 31/4745; A61K 31/5517; A61K 31/704; A61K 38/07; A61K 38/08; A61K 38/15; A61K 39/3955; A61K 2039/505; A61P 35/00; A61P 35/02; G01N 33/6872; G01N 33/6893; G01N 33/57484; G01N 33/6854
See application file for complete search history.

(56) References Cited

U.S. PATENT DOCUMENTS

| | | | |
|---|---|---|---|
| 5,545,806 | A | 8/1996 | Lonberg et al. |
| 5,569,825 | A | 10/1996 | Lonberg et al. |
| 5,633,425 | A | 5/1997 | Lonberg et al. |
| 5,661,016 | A | 8/1997 | Lonberg et al. |
| 2010/0254980 | A1 | 10/2010 | Cong et al. |
| 2013/0064823 | A1 | 3/2013 | Cong et al. |

FOREIGN PATENT DOCUMENTS

| | | | |
|---|---|---|---|
| CN | 103237811 | A | 8/2013 |
| WO | WO 2013/126911 | A1 | 8/2013 |
| WO | 2019084319 | A1 | 5/2019 |
| WO | WO 2019/126401 | A1 | 6/2019 |
| WO | 2019159084 | A1 | 8/2019 |

OTHER PUBLICATIONS

McCarthy BJ, Hill AS. Altering the fine specificity of an anti-Legionella single chain antibody by a single amino acid insertion. J Immunol Methods. May 1, 2001;251(1-2):137-49. (Year: 2001).*
Lin et al. Improved affinity of a chicken single-chain antibody to avian infectious bronchitis virus by site-directed mutagenesis of complementarity-determining region H3. African Journal of Biotechnology, 10(79):18294-18302, 2011. (Year: 2011).*

(Continued)

*Primary Examiner* — Sean E Aeder
*Assistant Examiner* — Yie Chia Lee
(74) *Attorney, Agent, or Firm* — Baker Botts L.L.P.

(57) ABSTRACT

Provided herein are antibodies that specifically bind LRP6 and method of use thereof.

16 Claims, 11 Drawing Sheets

Specification includes a Sequence Listing.

(56) References Cited

OTHER PUBLICATIONS

Mariuzza (Annu. Rev. Biophys. Biophys. Chem., 16: 139-159, 1987).*

Extended European Search Report issued in European Application No. 20851600.5 dated Jul. 26, 2023 (11 pages).

Yasui, N. et al., "Detection of endogenous LRP6 expressed on human cells by monoclonal antibodies specific for the native conformation", Journal of Immunological Methods, Jan. 31, 2010, pp. 153-160, vol. 352, Nos. 1-2, Elsevier B.V., XP026808319 (8 pages).

Ettenberg, S.A. et al. "Inhibition of Tumorigenesis Driven by Different Wnt Proteins Requires Blockade of Distinct Ligand-Binding Regions by LRP6 Antibodies". Proc Natl Acad Sci USA. 16, Aug. 2010, vol. 107, No. 35, pp. 15473-15478.

Gong, Y. et al. "Wnt Isoform-Specific Interactions with Coreceptor Specify Inhibition or Potentiation of Signaling by LRP6 Antibodies". PLoS One. Sep. 13, 2010, vol. 5, No. 9, e12682.

International Search Report and Written Opinion for PCT/CA2020/051120, dated Oct. 20, 2020.

Tao, Y. et al. "Tailored Tetravalent Antibodies Potently and Specifically Activate Wnt/Frizzled pathways in Cells, Organoids and Mice". Elife. Aug. 27, 2019, vol. 8, c46134.

Japanese-language Office Action issued in Japanese Application No. 2022-509039 dated Sep. 19, 2024, with English translation (19 pages).

Japanese-language Office Action issued in Japanese Application No. 2022-509039 dated Apr. 3, 2025, with English translation (6 pages).

* cited by examiner

| Clone ID | CDR-L1 | CDR-L2 | CDR-L3 | CDR-H1 | CDR-H2 | CDR-H3 | Epitope Group |
|----------|--------|--------|--------|--------|--------|--------|---------------|
| LRP6 - A1 | SVSSA (SEQ ID NO: 14) | SASSLYS (SEQ ID NO: 15) | YYWPI (SEQ ID NO: 20) | LSYYYI (SEQ ID NO: 2) | SIYSSYGYTS (SEQ ID NO: 6) | TVRGSKKPYFSGWAM (SEQ ID NO: 10) | 1 |
| LRP6 - A10 | SVSSA (SEQ ID NO: 14) | SASSLYS (SEQ ID NO: 15) | YSWGPF (SEQ ID NO: 17) | ISYSSI (SEQ ID NO: 25) | YISSYYGYTY (SEQ ID NO: 7) | AHYFPWAGAM (SEQ ID NO: 11) | 2 |
| LRP6 - B6 | SVSSA (SEQ ID NO: 14) | SASSLYS (SEQ ID NO: 15) | YYFLI (SEQ ID NO: 18) | ISYSSI (SEQ ID NO: 25) | SISPYYGYTY (SEQ ID NO: 8) | SSYFPWFSAM (SEQ ID NO: 12) | 2 |
| LRP6 - E3 | SVSSA (SEQ ID NO: 14) | SASSLYS (SEQ ID NO: 15) | AGSAPYHLI (SEQ ID NO: 19) | LYYYSM (SEQ ID NO: 4) | SIYSSYGYTY (SEQ ID NO: 9) | YAGVYYYPWAYYGWPFSGL (SEQ ID NO: 13) | 1 |
| LRP6 - G3 | SVSSA (SEQ ID NO: 14) | SASSLYS (SEQ ID NO: 15) | YYWPI (SEQ ID NO: 20) | ISSYYI (SEQ ID NO: 5) | SIYSSYGYTS (SEQ ID NO: 6) | TVRGSKKPYFSGWAM (SEQ ID NO: 10) | 1 |
| LRP6 - G9 | SVSSA (SEQ ID NO: 14) | SASSLYS (SEQ ID NO: 15) | YYWPI (SEQ ID NO: 20) | IYSYYI (SEQ ID NO: 26) | SIYSSYSYTS (SEQ ID NO: 27) | TVRGSKKPYFSGWAM (SEQ ID NO: 10) | 1 |

B

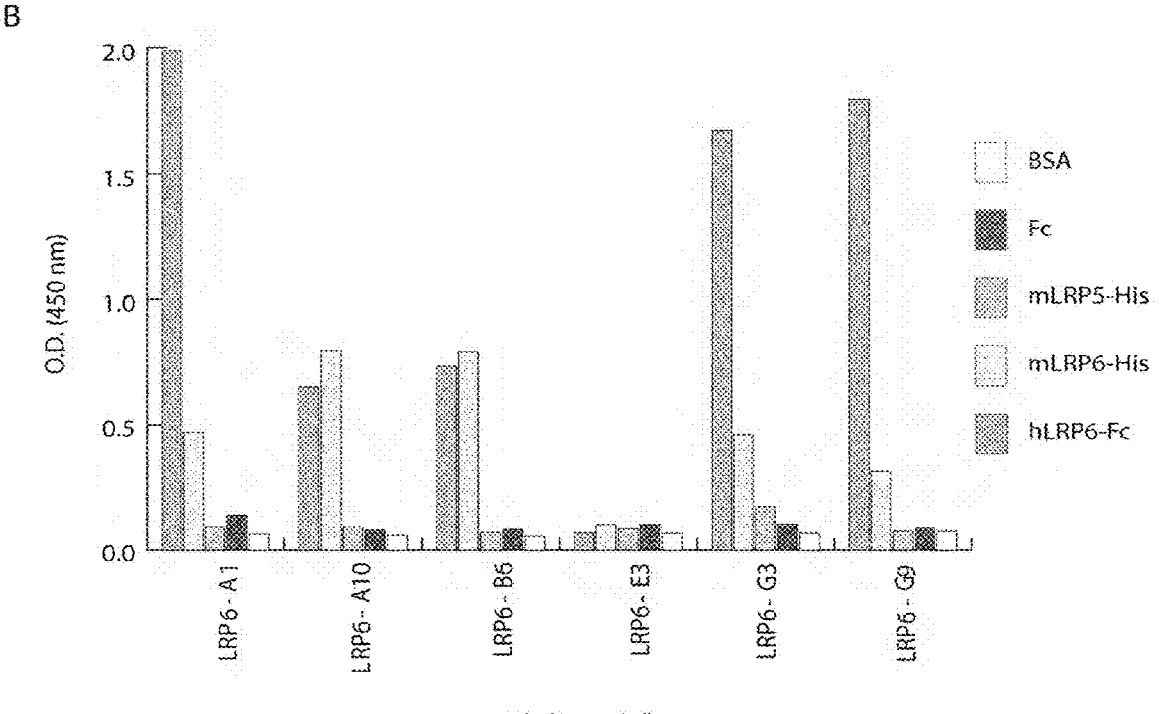

N.S. IgG1          LRP6 - A1          LRP6 - A10

LRP6 - B6          LRP6 - G3          LRP6 - G9

2nd only
IgG1

Figure 3
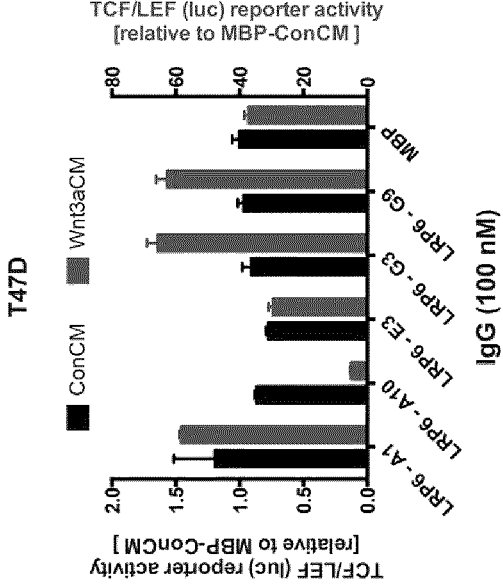
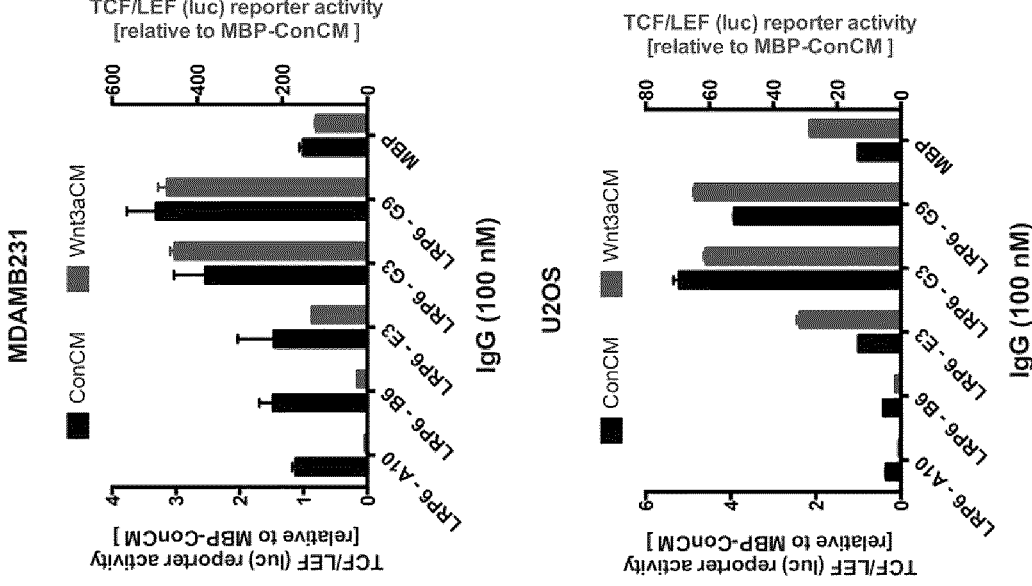

Figure 4
A
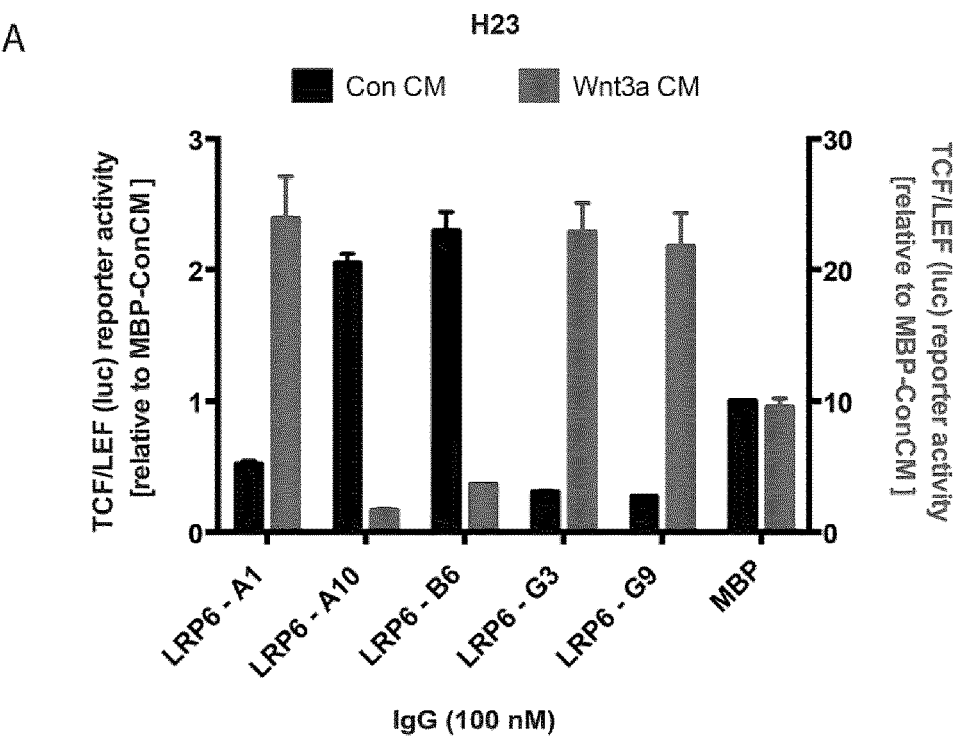
B
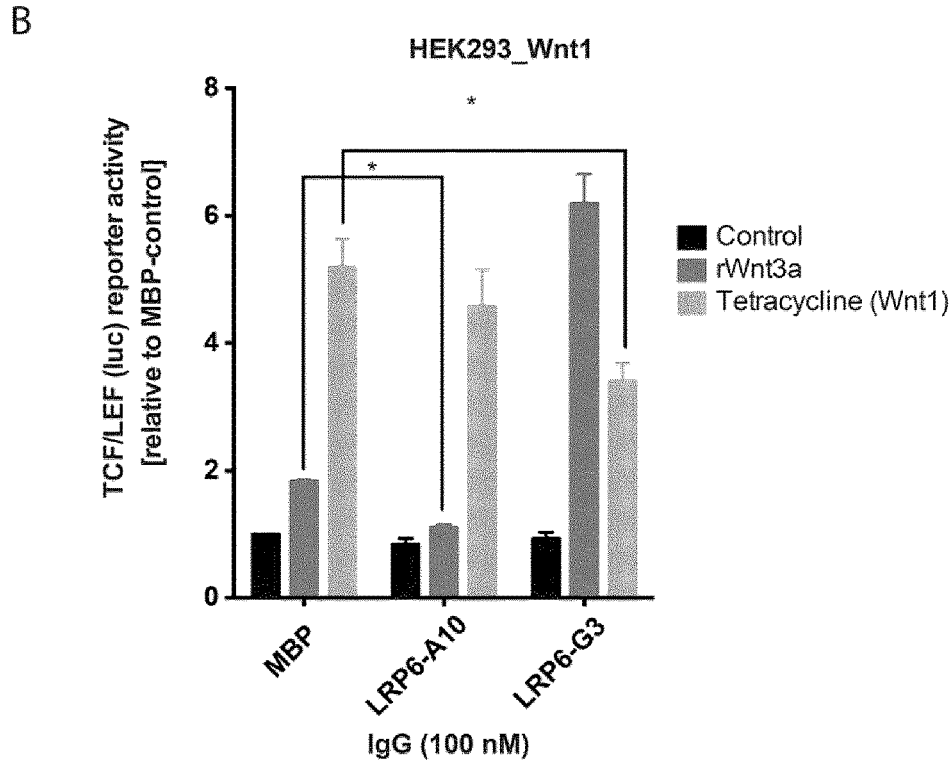

Figure 5
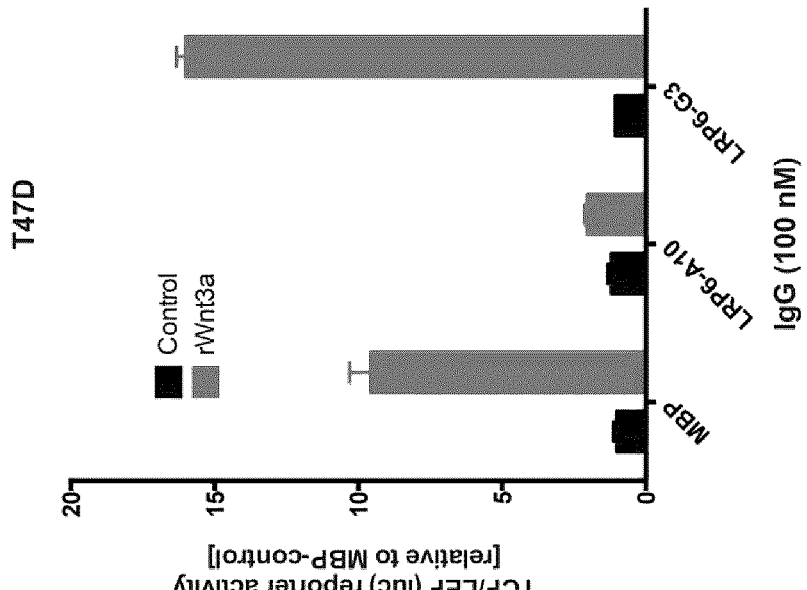
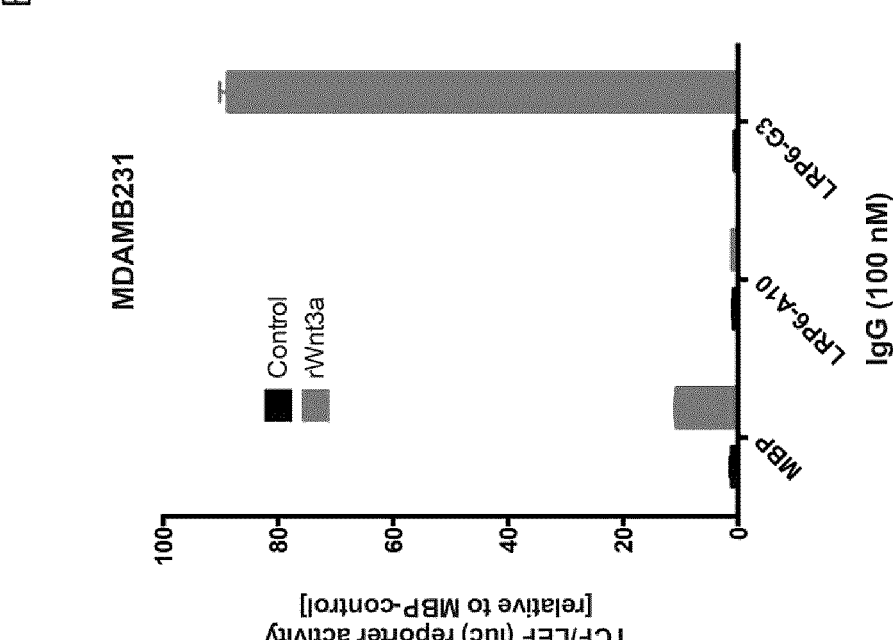

Figure 6
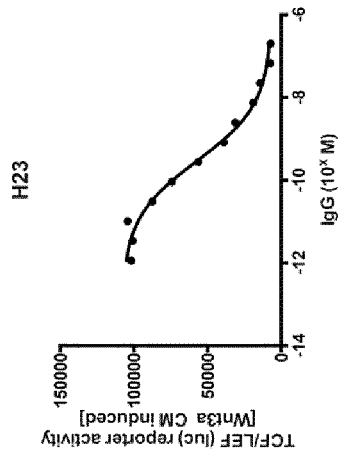
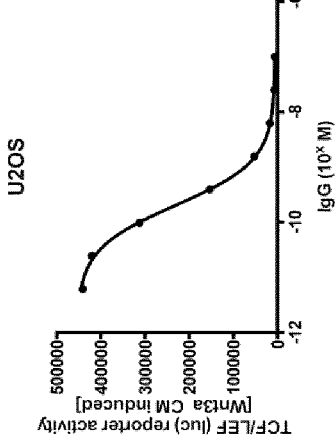
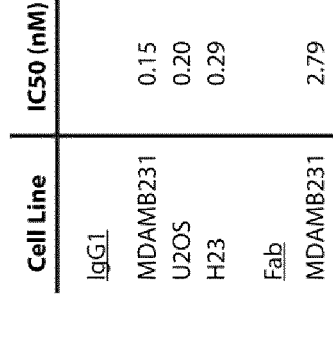
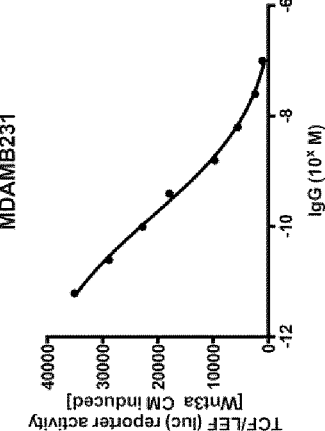
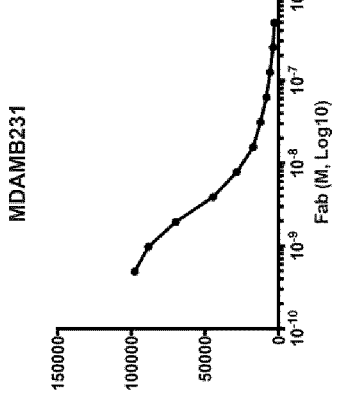

Figure 7
A
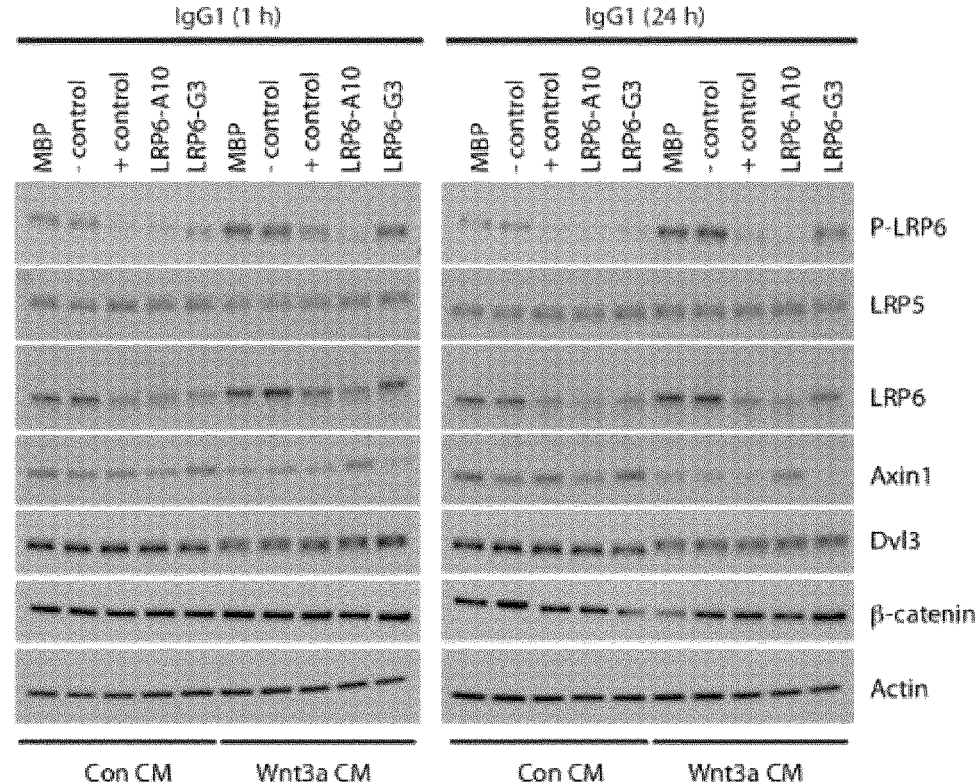
B
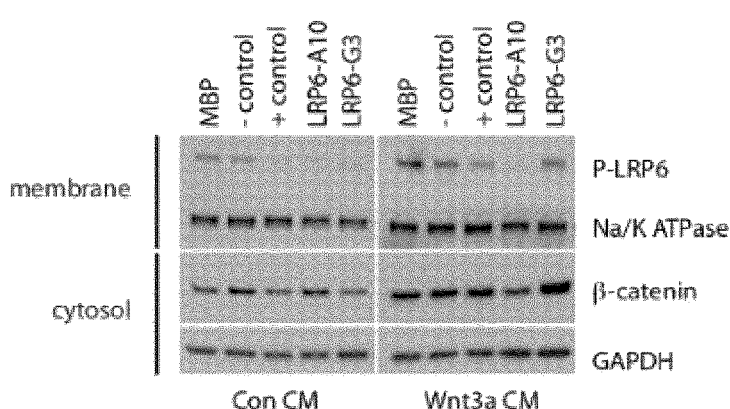

Figure 11

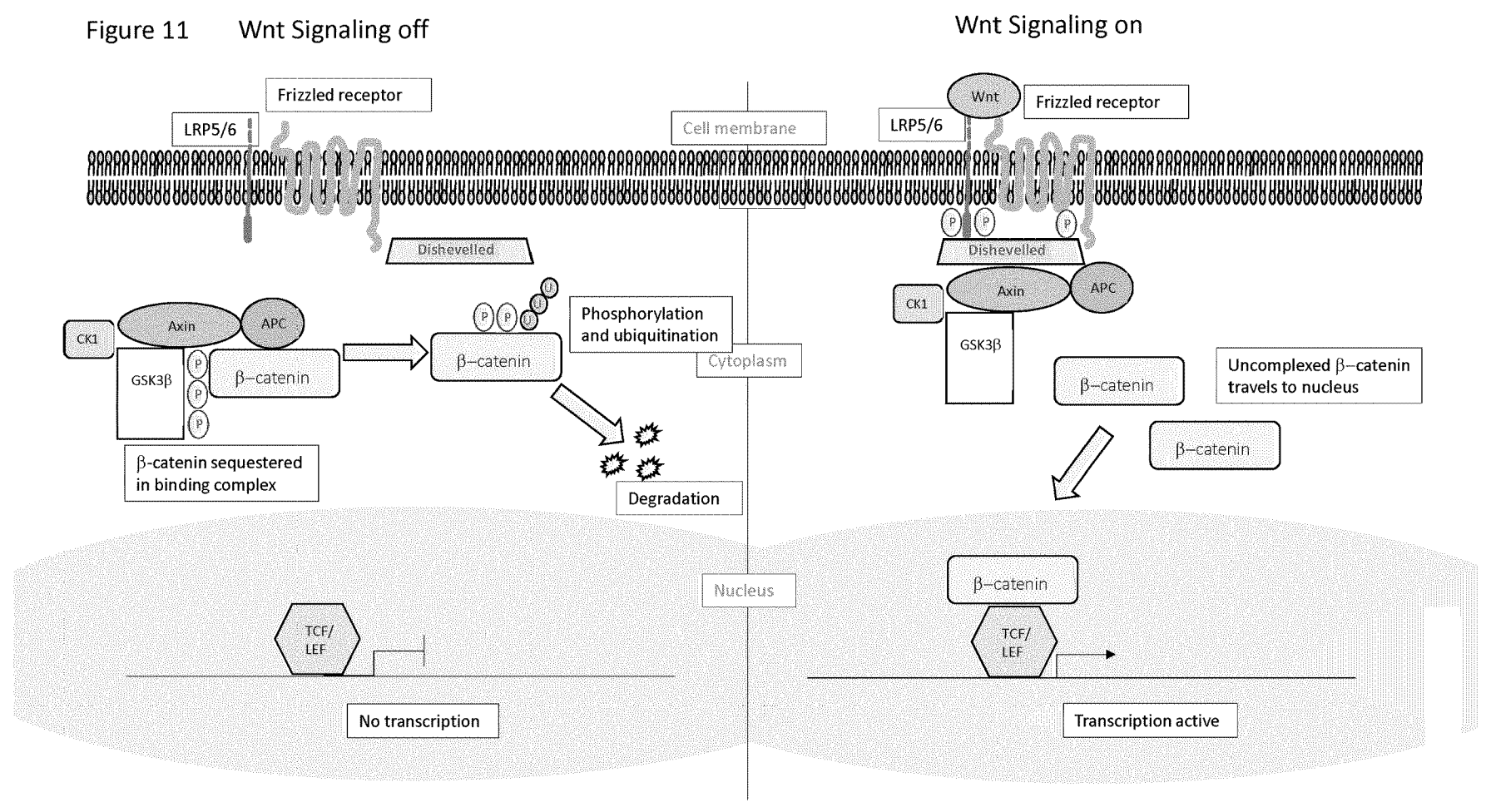

Wnt Signaling on

Wnt Signaling off

Frizzled receptor

LRP5/6

Cell membrane

Cytoplasm

Nucleus

Frizzled receptor

Wnt

LRP5/6

Dishevelled

APC

Axin

GSK3β

CK1

Uncomplexed β–catenin travels to nucleus

β–catenin

β–catenin

β–catenin

TCF/LEF

Transcription active

Dishevelled

APC

Axin

GSK3β

CK1

β–catenin

Phosphorylation and ubiquitination

Degradation

β–catenin sequestered in binding complex

TCF/LEF

No transcription

SEQUENCE LISTING

```
<160> NUMBER OF SEQ ID NOS: 47

<210> SEQ ID NO 1
<211> LENGTH: 7
<212> TYPE: PRT
<213> ORGANISM: Unknown
<220> FEATURE:
<223> OTHER INFORMATION: Description of Unknown:
      LRP5/6 phosphorylation site sequence
<220> FEATURE:
<221> NAME/KEY: MOD_RES
<222> LOCATION: (6)..(6)
<223> OTHER INFORMATION: Any amino acid

<400> SEQUENCE: 1

Pro Pro Pro Ser Pro Xaa Ser
1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Leu Ser Tyr Tyr Tyr Ile
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 3

Ile Ala Ser Tyr Ser Ser Ile
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Leu Tyr Tyr Tyr Ser Met
1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ile Ser Ser Tyr Tyr Ile
1               5

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Ile Tyr Ser Ser Tyr Gly Tyr Thr Ser
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Tyr Ile Ser Ser Tyr Tyr Gly Tyr Thr Tyr
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ser Ile Ser Pro Tyr Tyr Gly Tyr Thr Tyr
1               5                   10

<210> SEQ ID NO 9
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser Ile Tyr Ser Ser Tyr Gly Tyr Thr Tyr
1               5                   10

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Thr Val Arg Gly Ser Lys Lys Pro Tyr Phe Ser Gly Trp Ala Met
1               5                   10                  15

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala His Tyr Phe Pro Trp Ala Gly Ala Met
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ser Ser Tyr Phe Pro Trp Phe Ser Ala Met
1               5                   10

<210> SEQ ID NO 13
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Tyr Ala Gly Tyr Tyr Tyr Tyr Pro Trp Ala Tyr Tyr Gly Trp Pro Phe
1               5                   10                  15

Ser Gly Leu

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14
```

Ser Val Ser Ser Ala
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ser Ala Ser Ser Leu Tyr Ser
1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Tyr Tyr Ser Pro Ile
1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Tyr Ser Trp Gly Pro Phe
1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Tyr Tyr Phe Leu Ile
1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Gly Ser Ala Pro Tyr His Leu Ile
1               5

<210> SEQ ID NO 20
<211> LENGTH: 5
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 20

Tyr Tyr Trp Pro Ile
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ala Ala Tyr His Trp Pro Pro Leu Phe
1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Leu Tyr Tyr Thr Asp Met
1               5

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ser Ile Ser Leu Phe Phe Gly Tyr Val Ser
1               5                   10

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Tyr Leu Ala Met
1

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ile Ser Tyr Ser Ser Ile
1               5
```

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 26

Ile Tyr Ser Tyr Tyr Ile
1               5

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 27

Ser Ile Tyr Ser Ser Tyr Ser Tyr Thr Ser
1               5                   10

<210> SEQ ID NO 28
<211> LENGTH: 378
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 28
gaggttcagc tggtggagtc tggcggtggc ctggtgcagc cagggggctc actccgtttg      60
tcctgtgcag cttctggctt caacctctct tattattata tccactgggt gcgtcaggcc     120
ccgggtaagg gcctggaatg ggttgcatct atttattctt cttatggcta tacttcttat     180
gccgatagcg tcaagggccg tttcactata agcgcagaca catccaaaaa cacagcctac     240
ctacaaatga acagcttaag agctgaggac actgccgtct attattgtgc tcgcactgtt     300
cgtggatcca aaaaaccgta cttctctggt tgggctatgg actactgggg tcaaggaacc     360
ctggtcaccg tctcctcg                                                   378

<210> SEQ ID NO 29
<211> LENGTH: 126
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Ser Tyr Tyr
            20                  25                  30

Tyr Ile His Trp Val Arg Gln Ala Pro Gly Lys Gly Leu Glu Trp Val
        35                  40                  45

Ala Ser Ile Tyr Ser Ser Tyr Gly Tyr Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

-continued

```
Leu Gln Met Asn Ser Leu Arg Ala Glu Asp Thr Ala Val Tyr Tyr Cys
                85                  90                  95

Ala Arg Thr Val Arg Gly Ser Lys Lys Pro Tyr Phe Ser Gly Trp Ala
            100                 105                 110

Met Asp Tyr Trp Gly Gln Gly Thr Leu Val Thr Val Ser Ser
        115                 120                 125
```

```
<210> SEQ ID NO 30
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
gatatccaga tgacccagtc cccgagctcc ctgtccgcct ctgtgggcga tagggtcacc      60
atcacctgcc gtgccagtca gtccgtgtcc agcgctgtag cctggtatca acagaaacca     120
ggaaaagctc cgaagcttct gatttactcg gcatccagcc tctactctgg agtcccttct     180
cgcttctctg gtagccgttc cgggacggat ttcactctga ccatcagcag tctgcagccg     240
gaagacttcg caacttatta ctgtcagcaa tactactggc cgatcacgtt cggacagggt     300
accaaggtgg agatcaaacg t                                               321
```

```
<210> SEQ ID NO 31
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Trp Pro Ile Thr
                85                  90                  95

Phe Gly Gln Gly Thr Lys Val Glu Ile Lys Arg
            100                 105
```

```
<210> SEQ ID NO 32
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
gaggttcagc tggtggagtc tggcggtggc ctggtgcagc caggggggctc actccgtttg      60 tcctgtgcag cttctggctt caacatctct tattcttcta ccactgggt gcgtcaggcc     120
```

```
ccgggtaagg gcctggaatg ggttgcatat atttcttctt attatggcta tacttattat        180
gccgatagcg tcaagggccg tttcactata agcgcagaca catccaaaaa cacagcctac        240
ctacaaatga acagcttaag agctgaggac actgccgtct attattgtgc tcgcgctcat        300
tacttcccgt gggctggtgc tatggactac tggggtcaag aaccctggt caccgtctcc         360 tcg                                                                      363
```

```
<210> SEQ ID NO 33
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Tyr Ser
            20                  25                  30

Ser Ile His Trp Val Arg Gln Ala Pro Gly Lys Gly Leu Glu Trp Val
        35                  40                  45

Ala Tyr Ile Ser Ser Tyr Tyr Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ala His Tyr Phe Pro Trp Ala Gly Ala Met Asp Tyr Trp Gly
            100                 105                 110

Gln Gly Thr Leu Val Thr Val Ser Ser
        115                 120
```

```
<210> SEQ ID NO 34
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
gatatccaga tgacccagtc cccgagctcc ctgtccgcct ctgtgggcga tagggtcacc        60
atcacctgcc gtgccagtca gtccgtgtcc agcgctgtag cctggtatca acagaaacca       120
ggaaaagctc cgaagcttct gatttactcg gcatccagcc tctactctgg agtcccttct       180
cgcttctctg gtagccgttc cgggacggat ttcactctga ccatcagcag tctgcagccg       240
gaagacttcg caacttatta ctgtcagcaa tactcttggg tccgttcac gttcggacag        300 ggtaccaagg tggagatcaa acgt                                              324
```

```
<210> SEQ ID NO 35
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35
```

-continued

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Trp Gly Pro Phe
                85                  90                  95

Thr Phe Gly Gln Gly Thr Lys Val Glu Ile Lys Arg
            100                 105
```

```
<210> SEQ ID NO 36
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
gaggttcagc tggtggagtc tggcggtggc ctggtgcagc caggggggctc actccgtttg      60 tcctgtgcag cttctggctt caacatctct tattcttcta tccactgggt gcgtcaggcc     120
ccgggtaagg gcctggaatg ggttgcatct atttctcctt attatggcta tacttattat     180
gccgatagcg tcaagggccg tttcactata agcgcagaca catccaaaaa cacagcctac     240
ctacaaatga acagcttaag agctgaggac actgccgtct attattgtgc tcgctcttct     300
tacttcccgt ggttctctgc tatggactac tggggtcaag aaccctggt caccgtctcc     360 tcg                                                                  363
```

```
<210> SEQ ID NO 37
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Tyr Ser
            20                  25                  30

Ser Ile His Trp Val Arg Gln Ala Pro Gly Lys Gly Leu Glu Trp Val
        35                  40                  45

Ala Ser Ile Ser Pro Tyr Tyr Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Tyr Phe Pro Trp Phe Ser Ala Met Asp Tyr Trp Gly
            100                 105                 110

Gln Gly Thr Leu Val Thr Val Ser Ser
```

-continued

```
          115                 120

<210> SEQ ID NO 38
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
gatatccaga tgacccagtc cccgagctcc ctgtccgcct ctgtgggcga tagggtcacc        60
atcacctgcc gtgccagtca gtccgtgtcc agcgctgtag cctggtatca acagaaacca       120
ggaaaagctc cgaagcttct gatttactcg gcatccagcc tctactctgg agtcccttct       180
cgcttctctg gtagccgttc cgggacggat ttcactctga ccatcagcag tctgcagccg       240
gaagacttcg caacttatta ctgtcagcaa tactacttcc tgatcacgtt cggacagggt       300
accaaggtgg agatcaaacg t                                                 321

<210> SEQ ID NO 39
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
                20                  25                  30

Val Ala Trp Tyr Gln Gln Lys Pro Gly Lys Ala Pro Lys Leu Leu Ile
            35                  40                  45

Tyr Ser Ala Ser Ser Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Phe Leu Ile Thr
                85                  90                  95

Phe Gly Gln Gly Thr Lys Val Glu Ile Lys Arg
            100                 105

<210> SEQ ID NO 40
<211> LENGTH: 390
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
gaggttcagc tggtggagtc tggcggtggc ctggtgcagc cagggggctc actccgtttg        60
tcctgtgcag cttctggctt caacctctat tattattcta tgcactgggt gcgtcaggcc       120
ccgggtaagg gcctggaatg ggttgcatct atttattctt cttatggcta tacttattat       180
gccgatagcg tcaagggccg tttcactata agcgcagaca catccaaaaa cacagcctac       240
ctacaaatga acagcttaag agctgaggac actgccgtct attattgtgc tcgctacgct       300
ggttactact actacccgtg ggcttactac ggttggccgt tctctggttt ggactactgg       360
```

-continued

```
ggtcaaggaa ccctggtcac cgtctcctcg                                    390

<210> SEQ ID NO 41
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Tyr Tyr
            20                  25                  30

Ser Met His Trp Val Arg Gln Ala Pro Gly Lys Gly Leu Glu Trp Val
        35                  40                  45

Ala Ser Ile Tyr Ser Ser Tyr Gly Tyr Thr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Ala Gly Tyr Tyr Tyr Pro Trp Ala Tyr Tyr Gly Trp
            100                 105                 110

Pro Phe Ser Gly Leu Asp Tyr Trp Gly Gln Gly Thr Leu Val Thr Val
        115                 120                 125

Ser Ser
    130

<210> SEQ ID NO 42
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
gatatccaga tgacccagtc cccgagctcc ctgtccgcct ctgtgggcga tagggtcacc     60
atcacctgcc gtgccagtca gtccgtgtcc agcgctgtag cctggtatca acagaaacca    120
ggaaaagctc cgaagcttct gatttactcg gcatccagcc tctactctgg agtcccttct    180
cgcttctctg gtagccgttc cgggacggat ttcactctga ccatcagcag tctgcagccg    240
gaagacttcg caacttatta ctgtcagcaa gctggttctg ctccgtacca tctgatcacg    300
ttcggacagg gtaccaaggt ggagatcaaa cgt                                 333

<210> SEQ ID NO 43
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
```

-continued

```
               20                  25                  30

Val Ala Trp Tyr Gln Gln Lys Pro Gly Lys Ala Pro Lys Leu Leu Ile
           35                  40                  45

Tyr Ser Ala Ser Ser Leu Tyr Ser Gly Val Pro Ser Arg Phe Ser Gly
       50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Gly Ser Ala Pro Tyr
               85                  90                  95

His Leu Ile Thr Phe Gly Gln Gly Thr Lys Val Glu Ile Lys Arg
           100                 105                 110

<210> SEQ ID NO 44
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
gaggttcagc tggtggagtc tggcggtggc ctggtgcagc caggggggctc actccgtttg      60 tcctgtgcag cttctggctt caacatctct tcttattata tccactgggt gcgtcaggcc     120
ccgggtaagg gcctggaatg ggttgcatct atttattctt cttatggcta tacttcttat     180
gccgatagcg tcaagggccg tttcactata agcgcagaca catccaaaaa cacagcctac     240
ctacaaatga acagcttaag agctgaggac actgccgtct attattgtgc tcgcactgtt     300
cgtggatcca aaaaaccgta cttctctggt tgggctatgg actactgggg tcaaggaacc     360
ctggtcaccg tctcctcg                                                   378

<210> SEQ ID NO 45
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Ser Tyr
           20                  25                  30

Tyr Ile His Trp Val Arg Gln Ala Pro Gly Lys Gly Leu Glu Trp Val
       35                  40                  45

Ala Ser Ile Tyr Ser Ser Tyr Gly Tyr Thr Ser Tyr Ala Asp Ser Val
       50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
               85                  90                  95

Ala Arg Thr Val Arg Gly Ser Lys Lys Pro Tyr Phe Ser Gly Trp Ala
           100                 105                 110

Met Asp Tyr Trp Gly Gln Gly Thr Leu Val Thr Val Ser Ser
       115                 120                 125

<210> SEQ ID NO 46
```

-continued

```
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
gaggttcagc tggtggagtc tggcggtggc ctggtgcagc caggggggctc actccgtttg       60 tcctgtgcag cttctggctt caacatctat tcttattata tccactgggt gcgtcaggcc      120
ccgggtaagg gcctggaatg ggttgcatct atttattctt cttatagcta tacttcttat      180
gccgatagcg tcaagggccg tttcactata agcgcagaca catccaaaaa cacagcctac      240
ctacaaatga acagcttaag agctgaggac actgccgtct attattgtgc tcgcactgtt      300
cgtggatcca aaaaccgta cttctctggt tgggctatgg actactgggg tcaaggaacc      360
ctggtcaccg tctcctcg                                                   378

<210> SEQ ID NO 47
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Tyr Ser Tyr
            20                  25                  30

Tyr Ile His Trp Val Arg Gln Ala Pro Gly Lys Gly Leu Glu Trp Val
        35                  40                  45

Ala Ser Ile Tyr Ser Ser Tyr Ser Tyr Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Thr Val Arg Gly Ser Lys Lys Pro Tyr Phe Ser Gly Trp Ala
            100                 105                 110

Met Asp Tyr Trp Gly Gln Gly Thr Leu Val Thr Val Ser Ser
            115                 120                 125
```

1

ANTIBODIES THAT BIND TO LRP6 PROTEINS AND METHODS OF USE

REFERENCE TO RELATED APPLICATIONS

This application claims the benefit of the priority dates of U.S. provisional application 62/886,918, filed Aug. 14, 2019, the contents of which are incorporated herein by reference in its entirety.

STATEMENT AS TO FEDERALLY SPONSORED RESEARCH

None.

THE NAMES OF THE PARTIES TO A JOINT RESEARCH AGREEMENT

None.

SEQUENCE LISTING

The instant application contains a Sequence Listing which has been submitted electronically in ASCII format and is hereby incorporated by reference in its entirety. Said ASCII copy, created on Aug. 13, 2020, is named 27690-P62374PC00_MODM-006-PCT_SL.txt and is 24,580 bytes in size.

BACKGROUND

Wnt signaling has a crucial role in the regulation of various cellular processes such as cell fate determination, proliferation, survival, polarity and migration[1]. Perturbations, either as a result of altered expression or mutations in the Wnt signaling pathway have been implicated in defects in embryonic development as well as in various pathologies such as cancer and osteoporosis[2-4]. Wnt signaling leads to the activation of the canonical and non-canonical signaling pathways 1,5. The non-canonical pathway activates signaling molecules that do not involve the nucleus or transcription but rather activate cytoplasmic signals that regulate the cytoskeleton and calcium stores. This pathway primarily plays a role in regulating cell polarity or migration. The canonical pathway predominantly controls transcriptional activity by regulating the cytoplasmic levels of beta-catenin. In unstimulated conditions, beta-catenin is associated with a destruction complex, comprised of Axin, APC, CK1 and GSK3b, which results in the phosphorylation, ubiquitylation and proteasomal degradation of beta-catenin. Wnt signaling destabilizes this complex, resulting in the accumulation of "free" beta-catenin in the cytosol that translocates to the nucleus and acts as a co-activator for TCF/LEF mediated transcription. Wnts bind to the frizzled family of seven transmembrane domain receptors as well as to either LRP5 or LRP6 leading to the initiation of the canonical signaling pathway[6,7].

LRP5 and LRP6 are functionally redundant single-pass transmembrane receptors that share approximately 70% homology. Binding of Wnt ligands to Fzd and LRP5/6 leads to the recruitment of the destruction complex and Dishevelled (Dsh/Dvl) and the phosphorylation of LRP5/6 on PPPSPxS motifs (SEQ ID NO: 1) located in the intracellular domain[8]. This phosphorylation is mediated by GSK3b and CK1 which in turn results in diminished GSK3b activity, inhibiting beta-catenin phosphorylation and subsequent proteosomal degradation and enhanced TCF/LEF mediated transcriptional activity. LRP6 is widely expressed during embryonic development and in adult tissues. Mutations in LRP6 have been associated with bone mass diseases and several mouse models with LRP6 knockout or mutations exhibit alterations in bone development[9]. LRP6 expression has also been shown to be elevated in human malignant tissues and human cancer cell lines and Wnt signaling in such cell lines is dependent on the expression of LRP6[10-12]. This is further supported by the observation that LRP6 seems to be more effective than LRP5 in transducing the Wnt signal[13,14]. Because of the importance of LRP6 in regulating Wnt signaling and its established role in several human diseases, LRP6 is becoming an increasingly important target for therapeutic drug development. Recently, human synthetic antibodies targeting LRP6 revealed significant insight into how the Wnt ligands bind to different regions of the extracellular domain of LRP6. Moreover, the studies also showed that antagonizing antibodies to LRP6 could inhibit in vivo growth of Wnt-driven xenograft tumors[15,16]. However, these antibodies are still in the discovery stage and their potential as therapeutic agents in the clinic still remains to be elucidated. There is significant biology surrounding LRP6 and its role in Wnt signaling and in the pathogenesis of various diseases that still remains to be discovered and a deep toolbox of synthetic antibodies will help to systematically expose these roles and also provide additional targeted therapeutics.

Wnt signaling leads to the activation of the canonical and non-canonical signaling pathways. The non-canonical pathway activates signaling molecules that do not involve the nucleus or transcription but rather activate cytoplasmic signals that regulate the cytoskeleton and calcium levels. This pathway primarily plays a role in regulating cell polarity or migration.

The canonical pathway predominantly controls transcriptional activity by regulating the cytoplasmic levels of β-catenin. In unstimulated conditions, β-catenin is associated with a destruction complex, comprised of Axin, APC, CD1 and GSK β, which results in the phosphorylation, ubiquitylation and proteasomal degradation of β-catenin. Wnt signaling is active when Wnt binds to frizzled (FDZ), a 7-pass transmembrane receptor, and to a co-receptor low density lipoprotein receptor-related protein (either LRP5 or LRP6). This signaling destabilizes the complex, in part by attracting disheveled (Dsh/Dvl) to the plasma membrane, resulting in the accumulation of β-catenin, which then travels to the nucleus and activates TCF/LEF-mediated transcription.

The invention described below identifies a novel set of synthetic antibodies targeting the extracellular epitopes of LRP6, by taking advantage of state-of-the-art antibody phage display libraries and technology.

SUMMARY

In one aspect provided herein is an antibody that specifically binds LRP6, comprising a light chain variable region and/or a heavy chain variable region, the heavy chain variable region comprising complementarity determining regions CDR-H1, CDR-H2 and CDR-H3, the light chain variable region comprising complementarity determining region CDR-L1, CDR-L2 and CDR-L3, and with the amino acid sequences of said CDRs comprising or consisting of sequences selected from: CDR sequence sets of anti-LRP6 antibodies: LRP6-A1, LRP6-A10, LRP6-B6, LRP6-E3, LRP6-G3, and LRP6-G9. In one embodiment the amino acid sequences of said CDRs comprise or consist of sequences selected from the sequences as set forth below: CDR-H1 is selected from the group consisting of LSYYYI (SEQ ID NO: 2); ISYSSI (SEQ ID NO: 25); LYYYSM (SEQ ID NO: 4); ISSYYI (SEQ ID NO: 5) and IYSYYI (SEQ ID NO: 26); CDR-H2 is selected from the group consisting of SIYSSYGYTS (SEQ ID NO: 6); YISSYYGYTY (SEQ ID NO: 7); SISPYYGYTY (SEQ ID NO: 8); SIYSSYGYTY (SEQ ID NO: 9) and SIYSSYSYTS (SEQ ID NO: 27); CDR-H3 is selected from the group consisting of TVRG-SKKPYFSGWAM (SEQ ID NO: 10); AHYFPWAGAM (SEQ ID NO: 11); SSYFPWFSAM (SEQ ID NO: 12); YAGYYYYPWAYYGWPFSGL (SEQ ID NO: 13); TVRG-SKKPYFSGWAM (SEQ ID NO: 10); TVRGSKKPYFSG-WAM (SEQ ID NO: 10); CDR-L1 is SVSSA (SEQ ID NO: 14); CDR-L2 is SASSLYS (SEQ ID NO: 15); and/or CDR-L3 is selected from the group consisting of YYSPI (SEQ ID NO: 16), YSWGPF (SEQ ID NO: 17), YYFLI (SEQ ID NO: 18), AGSAPYHLI (SEQ ID NO: 19), and YYWPI (SEQ ID NO: 20). In another embodiment the antibody comprises a heavy chain variable region comprising: i) a heavy chain amino acid sequence as set forth in Table 2; ii) an amino acid sequence with at least 50%, at least 60%, at least 70%, at least 80%, at least 90%, at least 95%, at least 98% or at least 99% sequence identity to the heavy chain amino acid sequence as set forth in Table 2, wherein the CDR sequences are a CDR sequence set as set forth in Table 1, or iii) a conservatively substituted amino acid in another embodiment the antibody comprises a light chain variable region comprising: i) a light chain amino acid sequence as set forth in Table 2, ii) an amino acid sequence with at least 50%, at least 60%, at least 70%, at least 80%, at least 90%, at least 95%, at least 98% or at least 99% sequence identity to the light chain amino acid sequence as set forth in Table 2, wherein the CDR sequences are a CDR sequence set as set forth in Table 1, or iii) a conservatively substituted amino in another embodiment the CDR sequences are a full CDR sequence set selected from the antibodies identified in Table 1. In another embodiment the antibody cross-reacts with LRP5. In another embodiment the CDR sequences comprise a light chain or a heavy chain CDR sequence set selected from the antibodies identified in Table 1. In another embodiment antibody specifically binds LRP6. In another embodiment the CDR sequences are a CDR sequence set of an antibody selected from antibodies LRP6-A1, LRP6-A10, LRP6-B6, LRP6-E3, LRP6-G3, and LRP6-G9. In another embodiment the antibody blocks binding of Wnt ligands to the Wnt3a binding site of LRP6. In another embodiment the antibody blocks binding of Wnt ligands to the non-Wnt3a binding site of LRP6. In another embodiment the antibody is a monoclonal antibody. In another embodiment the antibody is a humanized antibody. In another embodiment wherein the antibody is a single chain antibody. In another embodiment the antibody is an antibody binding fragment selected from Fab, Fab', F(ab')2, scFv, dsFv, ds-scFv, dimers, nanobodies, minibodies, diabodies, and multimers thereof. In another embodiment the antibody is a bi-specific antibody. In another embodiment the antibody is a bi-specific antibody that further binds to FZD receptor. In another embodiment the antibody comprises a non-natural glycosylation pattern. In another embodiment the antibody comprises a cysteine substitution or addition, e.g., in the constant region or a framework region.

In another aspect provided herein is an immunoconjugate comprising an antibody as provided herein, and a detectable label or cytotoxic agent. In one embodiment the immuno conjugate comprises a cytotoxic agent selected from may-tansinoid, auristatin, dolastatin, tubulysin, cryptophycin, pyrrolobenzodiazepine (PBD) dimer, indolinobenzodiaz-epine dimer, alpha-amanitin, trichothene, SN-38, duocarmy-cin, CC1065, calicheamincin, an enediyne antibioatic, tax-ane, doxorubicin derivatives, anthracycline and stereoisomers, azanofide, isosteres, analogs or derivatives thereof.

In another aspect provided herein is a nucleic acid mol-ecule encoding an antibody as provided herein. In one embodiment one or more of the CDR sequences is/are encoded by a nucleic acid in Table 2. In another embodiment the antibody comprises a heavy chain variable region encoded by a nucleic acid comprising: i) a heavy chain nucleic acid sequence as set forth in Table 2; ii) a nucleotide sequence with at least 50%, at least 60%, at least 70%, at least 80%, at least 90%, at least 95%, at least 98% or at least 99% sequence identity to the heavy chain nucleic acid sequence as set forth in Table 2, wherein the CDR sequences are a CDR sequence set as set forth in Table 1, or iii) a codon degenerate nucleic acid sequence of i) wherein the CDR sequences are a CDR sequence set as set forth in Table 1. In another embodiment the antibody comprises a light chain variable region encoded by a nucleic acid comprising: i) a light chain nucleic acid sequence as set forth in Table 2, ii) a nucleic acid sequence with at least 50%, at least 60%, at least 70%, at least 80%, at least 90%, at least 95%, at least 98% or at least 99% sequence identity to the light chain nucleic acid sequence as set forth in Table 2, wherein the CDR sequences are a CDR sequence set as set forth in n Table 1, or iii) a codon degenerate nucleic acid sequence of i) wherein the CDR sequences are a CDR sequence set as set forth in Table 1.

In another aspect provided herein is a vector comprising an expression control sequence operatively linked to the nucleic acid as provided herein.

In another aspect provided herein is a host cell comprising recombinant nucleic acid molecule comprising an expres-sion control sequence operatively linked to the nucleic acid as provided herein. In one embodiment the cell is a Chinese Hamster Ovary (CHO) cell.

In another aspect provided herein is a host cell comprising a vector as provided herein.

In another aspect provided herein is a method for making an anti-LRP6 antibody comprising culturing a host cell as provided herein.

In another aspect provided herein is a composition com-prising an antibody, immunoconjugate, a nucleic acid mol-ecule, a vector, or a host cell as provided herein, optionally with a suitable diluent. In one embodiment the composition comprises one or more antibodies or immunoconjugates, optionally wherein the composition is a pharmaceutical composition.

In another aspect provided herein is a kit comprising an antibody, immunoconjugate, a nucleic acid molecule, a vector, or a host cell as provided herein.

In another aspect provided herein is a method of detecting LRP6 expression, the method comprising contacting a sample comprising one or more cells with one or more antibody or immunoconjugate as provided herein under conditions permissive for forming an antibody:cell complex and detecting the presence of any antibody complex. In one embodiment the detection is by immunofluorescence. In another embodiment the detection is by flow cytometry. In another embodiment the method is for detecting LRP4 expression and the antibody or immunoconjugate comprises a CDR sequence set corresponding to an antibody selected from LRP6-A1, LRP6-A10, LRP6-B6, LRP6-E3, LRP6-G3, and LRP6-G9.

In another aspect provided herein is a method of inhibiting Wnt ligand binding to an LRP6 receptor, disrupting a Wnt signaling pathway, inhibiting Wnt-induced transcriptional activity, inhibiting activation of disheveled, promoting preservation of the beta-catenin destruction complex, promoting accumulation of beta-catenin or inhibiting growth of a cell, the method comprising contacting a cell expressing a LRP6 receptor with an antibody or immunoconjugate as provided herein. In yet another aspect, provided is an antibody or immunoconjugate as provided herein for use in inhibiting Wnt ligand binding to an LRP6 receptor, disrupting a Wnt signaling pathway, inhibiting Wnt-induced transcriptional activity, inhibiting activation of disheveled, promoting preservation of the beta-catenin destruction complex, promoting accumulation of beta-catenin or inhibiting growth of a cell. In a further aspect, provided is a use of an antibody or immunoconjugate as provided herein for inhibiting Wnt ligand binding to an LRP6 receptor, disrupting a Wnt signaling pathway, inhibiting Wnt-induced transcriptional activity, inhibiting activation of disheveled, promoting preservation of the beta-catenin destruction complex, promoting accumulation of beta-catenin or inhibiting growth of a cell. In yet another aspect, provided is a use of an antibody or immunoconjugate as provided herein in the manufacture of a medicament for inhibiting Wnt ligand binding to an LRP6 receptor, disrupting a Wnt signaling pathway, inhibiting Wnt-induced transcriptional activity, inhibiting activation of disheveled, promoting preservation of the beta-catenin destruction complex, promoting accumulation of beta-catenin or inhibiting growth of a cell. In one embodiment the antibody or immunoconjugate blocks binding of a Wnt ligand to a Wnt3a binding site of LRP6. In another embodiment the antibody or immunoconjugate blocks binding of a Wnt ligand to a non-Wnt3a binding site of LRP6. In another embodiment antibody or immunoconjugate comprises a CDR sequence set corresponding to an antibody selected LRP6-A1, LRP6-A10, LRP6-B6, LRP6-E3, LRP6-G3, and LRP6-G9.

In another aspect provided herein is a method of treating cancer in a subject in need thereof comprising administering to the subject an effective amount of a pharmaceutical composition comprising an antibody or an immunoconjugate as provided herein. In another embodiment is a pharmaceutical composition comprising an antibody or an immunoconjugate as provided herein for use in treating cancer in a subject in need thereof. In a further embodiment is a use of a pharmaceutical composition comprising an antibody or an immunoconjugate as provided herein for treating cancer in a subject in need thereof. In yet another embodiment is a use of a pharmaceutical composition comprising an antibody or an immunoconjugate as provided herein in the manufacture of a medicament for treating cancer in a subject in need thereof. In one embodiment the cancer is selected from colon, lung, breast ovarian, endometrial, pancreas, stomach, liver, adrenocortical carcinoma and osteoblastoma cancer cells. In another embodiment the cancer is selected from acute myeloid leukemia, prostate cancer, glioblastoma, bladder cancer and cervical cancer. In another embodiment the method comprises administering to the subject first and second antibodies or antibody conjugates as provided herein, wherein the first blocks binding of a Wnt ligand to a Wnt3a binding site of LRP6, and the second blocks binding of a Wnt ligand to a non-Wnt3a binding site of LRP6. In another embodiment the first antibody or immunoconjugate comprises a CDR sequence set selected from antibodies LRP6-A10 or LRP6-B6 and the second antibody or immunoconjugate comprises a CDR sequence set selected from antibodies LRP6-A1, LRP6-A10, LRP6-B6, LRP6-E3, LRP6-G3, or LRP6-G9. In another embodiment the antibody or immunoconjugate that specifically binds LRP6 in at least one assay, and inhibits Wnt3a-induced signaling in at least one assay, optionally wherein the antibody or immunoconjugate is the antibody or immunoconjugate as provided herein. In another embodiment the antibody or immunoconjugate comprises a CDR sequence set corresponding to an antibody selected from LRP6-A1, LRP6-A10, LRP6-B6, LRP6-E3, LRP6-G3, and LRP6-G9.

In another aspect provided herein is a method of potentiating the signaling activity of Wnt-ligand binding to a Wnt3a binding site of LRP6 comprising contacting a cell expressing LRP6 with an antibody that blocks binding of Wnt ligands to the non-Wnt3a binding site of LRP6. In one embodiment the method is performed in vitro. In another embodiment the method is performed in vivo.

In another aspect provided herein is a method of potentiating the signaling activity of Wnt-ligand binding to a non-Wnt3a binding site of LRP6 by contacting a cell expressing LRP6 with an antibody that blocks binding of Wnt ligands to the Wnt3a binding site of LRP6. In one embodiment the method is performed in vitro. In another embodiment the method is performed in vivo.

BRIEF DESCRIPTION OF THE DRAWINGS

The accompanying drawings, which are incorporated herein and form a part of the specification, illustrate exemplary embodiments and, together with the description, further serve to enable a person skilled in the pertinent art to make and use these embodiments and others that will be apparent to those skilled in the art. The invention will be more particularly described in conjunction with the following drawings wherein:

FIGS. 1a and 1b show LRP six antibodies. (A) The amino acid sequences of the complementarity determining regions (CDR) of the heavy (H) and the light (L) chains are presented. The antibodies were grouped into unique epitopes as determined by competitive ELISAs. (B) Single-point ELISAs were performed on 96-well Maxisorb immune plates coated with the EDC's of mouse LRP5, mouse LRP6 and human LRP6 chimeras. The plates were incubated with the purified Fab or IgG1 at the concentrations indicated followed by incubation with horseradish peroxidase (HRP)-conjugated anti-kappa antibody. The wells were washed eight times followed by incubation with 3,3',5,5'-tetramethylbenzidine/$H_2O_2$ peroxidase (TMB) substrate for 5-10 min. The reaction was stopped by adding one M $H_3PO_4$ and the absorbance was measured spectrometrically at 450 nm in a microtiter plate reader.

FIGS. 3A-3C show the effect of LRP6 IgG's on transcriptional activity in cancer cells. TCF/LEF reporter assays were performed using the TOPflash (firefly luciferase gene) in (A) MDAMB231, (B) T407D and (C) U2OS cells. Cells were seeded in white-walled, white bottom-96 well plates in treated with the IgG at the indicated concentration for one H prior to stimulation with conditioned media. The cells were lysed 16-20 H post stimulation with conditioned media and reporter activity was assessed by measuring the luminescence signal generated by the addition of the firefly luminescence reagent. The values are normalized to the signal observed in cells treated with the negative control antibody, anti-MBP, and stimulated with ConCM. The data presented is representative of three independent experiments where each condition is an average of three replicates.

FIGS. 4A and 4B show the effect of LRP6 IgGs on transcriptional activity in cancer cells. TCF/LEF reporter assays were performed using the TOPflash (firefly luciferase gene) in (A) H23 cells treated with conditioned media or (B) HEK293_Wnt1 cells are stimulated with recombinant Wnt3a (500 ng/ml) or tetracycline (2 ng/ml). Reporter activity was assessed as described in the description of FIG. 3.

FIGS. 5A and 5B show the effect of LRP6 IgGs on transcriptional activity in cancer cells. TCF/LEF reporter assays were performed using the TOPflash (firefly luciferase gene) in (A) MDAMB231 and (B) T407D breast cancer cells treated with LRP 6-A10 and LRP 6-G3 IgG1 prior to stimulation with recombinant Wnt3a (500 ng/ml). Reporter activity was assessed as described in the description of FIG. 3.

FIGS. 6A-6C show the effect of LRP6-A10 IgG1 and Fab on transcriptional activity in cancer cells. Wnt3aCM induced TCF/LEF reporter assays were performed using the TOPflash (firefly luciferase gene) in MDAMB231, U2OS and H23 cancer cells pretreated with increasing concentrations of LRP6-A10 (A) IgG1 or (B) Fab protein. Reporter activity was assessed as described in the description of FIG. 3. (C) the IC50 was determined by non-linear regression analysis.

FIGS. 7A and 7B show the effect of LRP6 IgG1 on β-catenin signaling. The H23 cell line was pretreated with LRP6 IgGs (100 nM) for the time point indicated prior to stimulation with conditioned media. (A) total whole cell lysate or (B) membrane and cytosolic fractions were generated and separated by SDS-page. The PVDF membrane was cut and immunoblotted for phosphorylated LRP6, LRP5, LRP6, Axin1, Dvl3 and β-catenin. Actin was used as a loading control for whole cell lysate while Na/K ATPase and GAPDH were used as loading control for the membrane and cytosolic fractions, respectively.

FIG. 9 shows an analysis of IgG1 binding to cell-surface LRP6 by flow cytometry. LRP6 IgGs were tested for binding to the breast cancer cell line, MDAMB231. Binding of the anti-LRP6 IgG1 proteins was detected using an Alexa488-conjugated secondary antibody against F(ab')$_2$. The stained anti-LRP6 population is shown in green in the secondary only state population is shown filled in.

FIG. 11 shows a diagram of the Wnt canonical signaling pathway.

DETAILED DESCRIPTION

I. Definitions

Figure 2:
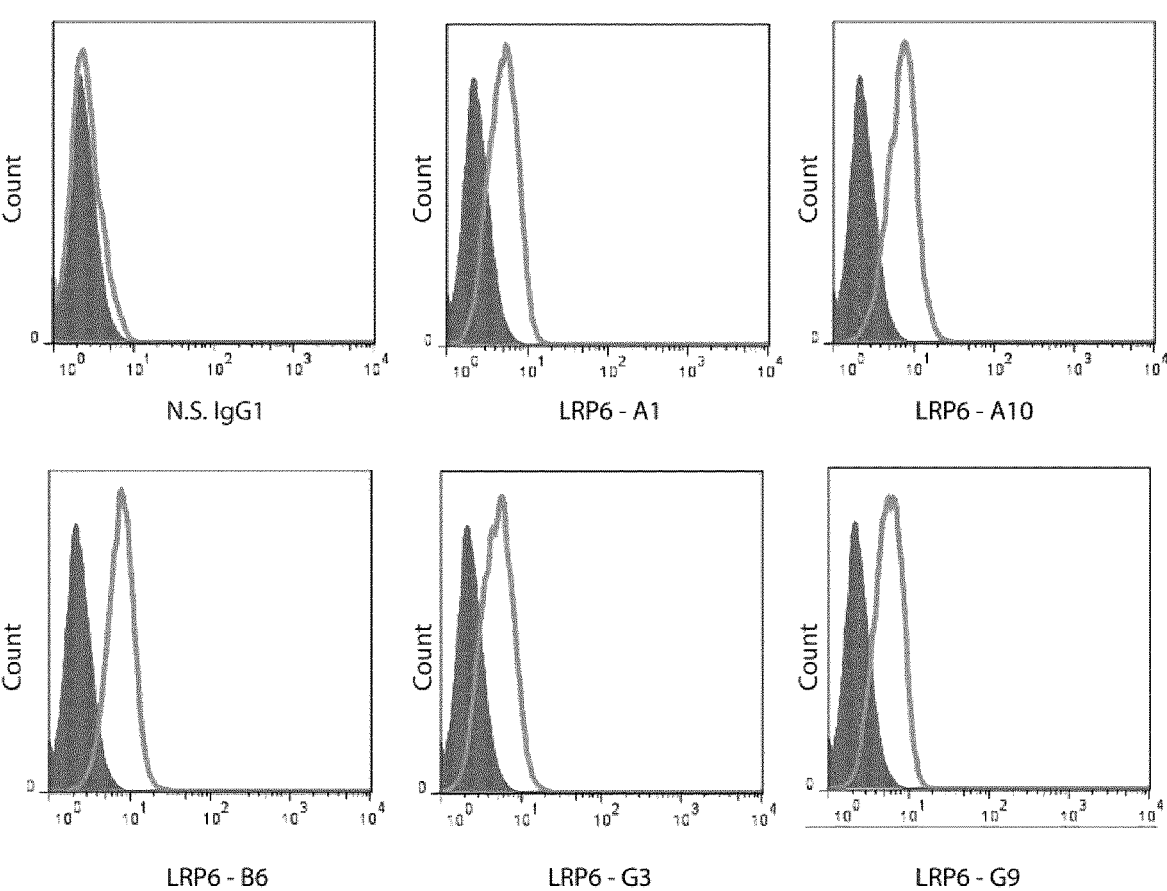
FIG. 2 shows analysis of IgG1 binding to sell-surface LRP 6 by flow cytometry. LRP6 IgG's were tested for binding to the NSCLC cell line, H23. Binding of the anti-LRP6 IgG1 proteins was detected using an Alexa488-conjugated secondary antibody against $F(ab')_2$. The stained anti-LRP6 population is shown in green in the secondary only state population is shown in field blue.

Unless otherwise defined, scientific and technical terms used in connection with the present disclosure shall have the meanings that are commonly understood by those of ordinary skill in the art. Further, unless otherwise required by context, singular terms shall include pluralities and plural terms shall include the singular. For example, the term "a cell" includes a single cell as well as a plurality or population of cells. Generally, nomenclatures utilized in connection with, and techniques of, cell and tissue culture, molecular biology, and protein and oligonucleotide or polynucleotide chemistry and hybridization described herein are those well-known and commonly used in the art (see, e.g. Green and Sambrook, 2012).

As used herein, the term "polypeptide" refers to a molecule having a sequence of natural and/or unnatural amino acids connected through peptide bonds. The term "peptide" refers to a short polypeptide, typically no more than 30 amino acids long. The amino acid sequence of a polypeptide is referred to as its "primary structure." The term "protein" refers to a polypeptide having a secondary, tertiary and/or quaternary structure, e.g., structures stabilized by hydrogen bonds, relationships between secondary structures and structures formed of more than one protein. Proteins can be further modified by other attached moieties such as carbohydrate (glycoproteins), lipids (lipoproteins) phosphate groups (phosphoproteins) and the like.

As used herein, an amino acid sequence "consists of" only the amino acids in that sequence.

As used herein, a first amino acid sequence "consists essentially of" a second amino acid sequence if the first amino acid sequence (1) comprises the second amino sequence and (2) is no more than 1, no more than 2 or no more than 3 amino acids longer than the second amino acid sequence.

As used herein, a first amino acid sequence is a "fragment" of a second amino acid sequence if the second amino acid sequence comprises the first amino acid sequence. In certain embodiments, a first amino acid sequence that is a fragment of a second amino acid sequence may have no more than any of 1, 2, 3, 4, 5, 6, 7, 8, 9 or 10 fewer amino acids than the second amino acid sequence.

As used herein, a "functional equivalent" of a reference amino acid sequence is a sequence that is not identical to the reference sequence, but that contains minor alterations such as, for example, insertion, deletion or substitution of one or a few amino acids. A functionally equivalent sequence retains the function (e.g., immunogenicity) of the reference sequence to which it is equivalent. If a functionally equivalent amino acid sequence contains substitution of one or more amino acids with respect to the reference sequence, these will generally be conservative amino acid substitutions.

As used herein, a "conservative amino acid substitution" is one in which one amino acid residue is replaced with another amino acid residue without abolishing the protein's desired properties. Suitable conservative amino acid substitutions can be made by substituting amino acids with similar hydrophobicity, polarity, and R-chain length for one another. See, e.g., Watson, et al., "Molecular Biology of the Gene," 4th Edition, 1987, The Benjamin/Cummings Pub. Co., Menlo Park, CA, p. 224. Examples of conservative amino acid substitution include the following (Note, some categories are not mutually exclusive):

| Conservative Substitutions | |
|---|---|
| Type of Amino Acid | Substitutable Amino Acids |
| Hydrophilic | Ala, Pro, Gly, Glu, Asp, Gln, Asn, Ser, Thr |
| Sulphydryl | Cys |
| Aliphatic (non-polar, hydrophobic) | Ala, Val, Ile, Leu, Met, Gly, Pro |
| Basic | Lys, Arg, His |
| Aromatic | Phe, Tyr, Trp |

As used herein, the term "substantially identical" refers to identity between a first amino acid sequence that contains a sufficient or minimum number of amino acid residues that are i) identical to, or ii) conservative substitutions of aligned amino acid residues in a second amino acid sequence such that the first and second amino acid sequences have a common structural domain and/or common functional activity and/or common immunogenicity. For example, amino acid sequences that contain a common structural or antigenic domain having at least about 90%, 91%, 92%, 93%, 94%, 95%, 96%, 97%, 98% or 99% identity are termed sufficiently or substantially identical. In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity, or encode polypeptides having the same immunogenic properties.

As used herein, the terms "antigen," "immunogen," and "antibody target," refer to a molecule, compound, or complex that is recognized by an antibody, i.e., can be bound by the antibody. The term can refer to any molecule that can be recognized by an antibody, e.g., a polypeptide, polynucleotide, carbohydrate, lipid, chemical moiety, or combinations thereof (e.g., phosphorylated or glycosylated polypeptides, etc.). One of skill will understand that the term does not indicate that the molecule is immunogenic in every context, but simply indicates that it can be targeted by an antibody.

As used herein, the term "epitope" refers to the localized site on an antigen that is recognized and bound by an antibody. Epitopes can include a few amino acids or portions of a few amino acids, e.g., 5 or 6, or more, e.g., 20 or more amino acids, or portions of those amino acids. In some cases, the epitope includes non-protein components, e.g., from a carbohydrate, nucleic acid, or lipid. In some cases, the epitope is a three-dimensional moiety. Thus, for example, where the target is a protein, the epitope can be comprised of consecutive amino acids, or amino acids from different parts of the protein that are brought into proximity by protein folding (e.g., a discontinuous epitope).

As used herein, the term "antibody" refers to an immunoglobulin that recognizes and specifically binds to a one or more target antigen(s), such as a protein, polypeptide, peptide, carbohydrate, polynucleotide, lipid or combinations thereof. This binding occurs through at least one antigen recognition site within the variable region of the immunoglobulin at one or more epitopes on the antigen. The variable region is most critical in binding specificity and affinity. As used herein, the term "antibody" encompasses intact polyclonal antibodies, intact monoclonal antibodies, antibody fragments, single chain Fv (scFv) mutants, multispecific antibodies, chimeric antibodies, humanized antibodies, human antibodies, hybrid antibodies, fusion proteins and any other immunoglobulin molecule comprising an antigen recognition site so long as the antibody exhibit the desired biological activity. Antibodies can be of (i) any of the five major classes of immunoglobulins, based on the identity of their heavy-chain constant domains—alpha (IgA), delta (IgD), epsilon (IgE), gamma (IgG) and mu (IgM), or (ii) subclasses (isotypes) thereof (E.g., IgG1, IgG2, IgG3, IgG4, IgA1 and IgA2). The light chains can be either lambda or kappa. Antibodies can be naked or conjugated to other molecules such as toxins, drugs, radioisotopes, chemotherapeutic agents, etc.

In one embodiment, an "intact antibody" comprises a tetramer composed of two identical pairs of polypeptide chains, each pair having one "light" (about 25 kD) and one "heavy" chain (about 50-70 kD). The heavy chain and light chains are connected through covalent and non-covalent bonds (e.g., disulfide linkage) that vary in number and amount between the various immunoglobulin classes. In one aspect, each chain comprises a variable region and a constant region. The antigen recognition site of the variable region is composed of hypervariable regions or complementarity determining regions (CDRs) and frameworks regions. The framework regions typically do not come into contact with the antigen but provide structural support for the CDRs. The constant region interacts with other immune cells of the body. Between the constant and variable region (IgG, IgD, IgA only but not IgM or IgE) is the hinge region in the center between the two heavy chains that provides flexibility to articulate antigen binding.

The following are a non-exhaustive list of different antibody forms, all retaining antigen binding activity:
(1) whole immunoglobulins (also referred to as "intact" antibodies) (two light chains and two heavy chains, e.g., a tetramer).
(2) an immunoglobulin polypeptide (a light chain or a heavy chain).
(3) an antibody fragment, such as Fv (a monovalent or bi-valent variable region fragment, and can encompass only the variable regions (e.g., $V_L$ and/or $V_H$), Fab ($V_L C_L$ $V_H C_H$), F(ab')2, Fv ($V_L V_H$), scFv (single chain Fv) (a polypeptide comprising a $V_L$ and $V_H$ joined by a linker, e.g., a peptide linker), (scFv)2, sc(Fv)2, bispecific sc(Fv)2, bispecific (scFv)2, minibody (sc(FV)2 fused to CH3 domain), triabody is trivalent sc(Fv)3 or trispecific sc(Fv)3
(4) a multivalent antibody (an antibody comprising binding regions that bind two different epitopes or proteins, e.g., "scorpion" antibody.
(5) a fusion protein comprising a binding portion of an immunoglobulin fused to another amino acid sequence (such as a fluorescent protein).

As used herein, the term "antibody fragment" refers to a part or portion of an antibody or antibody chain comprising fewer amino acid residues than an intact or complete antibody or antibody chain and which binds the antigen or competes with intact antibody. Fragments can be obtained via chemical or enzymatic treatment of an intact or complete antibody or antibody chain. Fragments can also be obtained by recombinant means. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, dsFv, ds-scFv, dimers, minibodies, diabodies, bispecific antibody fragments and other fragments can also be constructed by recombinant expression techniques.

While various antibody fragments are defined in terms of products of the digestion of an intact antibody, one of skill will appreciate that such fragments may also be synthesized de novo chemically or constructed and expressed using recombinant DNA methodology.

A single chain Fv (scFv) refers to a polypeptide comprising a $V_L$ and $V_H$ joined by a linker, e.g., a peptide linker. ScFvs can also be used to form tandem (or di-valent) scFvs or diabodies. Production and properties of tandem scFvs and diabodies are described, e.g., in Asano et al. (2011) *J Biol. Chem.* 286:1812; Kenanova et al. (2010) *Prot Eng Design Sel* 23:789; Asano et al. (2008) *Prot Eng Design Sel* 21:597.

Antibody fragments further include Fd (the portion of the heavy chain included in the Fab fragment) and single domain antibodies. A single domain antibody (sdAb) is a variable domain of either a heavy chain or a light chain, produced by recombinant methods.

The phrase "CDR sequence set" as used herein refers to the 3 heavy chain and/or 3 light chain CDRs of a particular antibody described herein. A "light chain" CDR sequence set refers to the light chain CDR sequences. A "heavy chain" CDR sequence set refers to the heavy chain CDR sequences. A "full" CDR sequence set refers to both heavy chain and light chain CDR sequences. For example, for antibody LRP6-A1, as shown in Table 1, the full CDR sequence set comprises or consists of SVSSA (SEQ ID NO: 14) (CDR L1), SASSLYS (SEQ ID NO: 15) (CDR L2), YYWPI (SEQ ID NO: 20) (CDR L3), LSYYYI (SEQ ID NO: 2) (CDR H1), SIYSSYGYTS (SEQ ID NO: 6) (CDR H2) and TVRG-SKKPYFSGWAM (SEQ ID NO: 10) (CDR H3). The CDR sequence for each CDR can, for example, comprise, consist essentially of, or consist of the CDRs in Table 1. CDRs are predicted based on IMGT sequence alignment.

As used herein, the term "monoclonal antibody" refers to a clonal preparation or composition of antibodies with a single binding specificity and affinity for a given epitope on an antigen ("monoclonal antibody composition"). A "polyclonal antibody" refers to a preparation or composition of antibodies that are raised against a single antigen, but with different binding specificities and affinities ("polyclonal antibody composition").

As used herein, the term "chimeric antibody" refers to an antibody having amino acid sequences derived from two or more species. In one embodiment, the variable region of both light and heavy chains correspond to the variable region of antibodies derived from one species of mammal (e.g., mouse, rat, rabbit, etc.) with the desired specificity, affinity and capability, while the constant region are homologous the sequence derived from another species (typically in the subject receiving the therapy, e.g., human) to avoid eliciting an immune response.

As used herein, the term "humanized antibody" refers to a chimeric antibody in which the CDRs, obtained from the VH and VL regions of a non-human antibody having the desired specificity, affinity and capability are grafted to a human framework sequence. In one embodiment, the framework residues of the humanized antibody are modified to refine and optimize the antibody specificity, affinity and capability. Humanization, i.e., substitution of non-human CDR sequences for the corresponding sequences of a human antibody, can be performed following the methods described in, e.g., U.S. Pat. Nos. 5,545,806; 5,569,825; 5,633,425; 5,661,016; Riechmann et al., Nature 332:323-327 (1988); Marks et al., Bio/Technology 10:779-783 (1992); Morrison, Nature 368:812-13 (1994); Fishwild et al., Nature Biotechnology 14:845-51 (1996).

As used herein, the term "human antibody" refers to an antibody produced by a human or an antibody having an amino acid sequence corresponding thereto made by any technique known in the art.

As used herein, the term "hybrid antibody" refers to antibody in which pairs of heavy and light chains form antibodies with different antigenic determinant regions are assembled together so that two different epitopes or two different antigens can be recognized and bound by the resulting tetramer. Hybrid antibodies can be bispecific (binding 2 distinct antigens or epitopes) or multispecific (>1 distinct antigen or epitope).

As used herein, an antibody is "monospecific" if all of its antigen binding sites bind to the same epitope.

As used herein, an antibody is "bispecific" if it has at least two different antigen binding sites which each bind to a different epitope or antigen.

As used herein, an antibody is "polyvalent" if it has more than one antigen binding site. For example, an antibody that is tetravalent has four antigen binding sites.

The specificity of the binding can be defined in terms of the comparative dissociation constants (Kd) of the antibody (or other targeting moiety) for target, as compared to the dissociation constant with respect to the antibody and other materials in the environment or unrelated molecules in general. A larger (higher) $K_d$ is a $K_d$ that describes a lower affinity interaction. Conversely a smaller (lower) $K_d$ is a $K_d$ that describes a higher affinity interaction or tighter binding. By way of example only, the $K_d$ for an antibody specifically binding to a target may be femtomolar, picomolar, nanomolar, or micromolar and the $K_d$ for the antibody binding to unrelated material may be millimolar or higher. Binding affinity can be in the micromolar range (kD=$10^{-4}$ to 101, nanomole range (kD=$10^{-7}$ M to $10^{-9}$ M), picomole range (kD=$10^{-10}$ M to $10^{-12}$ M), or femtomole range (kD=$10^{-13}$ M to $10^{-15}$ M).

As used herein, an antibody "binds" or "recognizes" an antigen or epitope if it binds the antigen or epitope with a Kd of less than $10^{-4}$M (i.e., in the micromolar range). The term "binds" with respect to a cell type (e.g., an antibody that binds cancer cells), typically indicates that an agent binds a majority of the cells in a pure population of those cells. For example, an antibody that binds a given cell type typically binds to at least ⅔ of the cells in a population of the indicated cells (e.g., 67, 75, 80, 85, 90, 91, 92, 93, 94, 95, 96, 97, 98, 99, or 100%). In some cases, binding to a polypeptide can be assayed by comparing binding of the antibody to a cell that presents the polypeptide to binding (or lack thereof) of the antibody to a cell that does not express the polypeptide. One of skill will recognize that some variability will arise depending on the method and/or threshold of determining binding. Affinity of an antibody for a target can be determined according to methods known in the art, e.g., as reviewed in Ernst et al. Determination of Equilibrium Dissociation Constants, *Therapeutic Monoclonal Antibodies* Miley & Sons ed. 2009).

As used herein, the term "greater affinity" as used herein refers to a relative degree of antibody binding where an antibody X binds to target Y more strongly ($K_{on}$) and/or with a smaller dissociation constant ($K_{off}$) than to target Z, and in this context antibody X has a greater affinity for target Y than for Z. Likewise, the term "lesser affinity" herein refers to a degree of antibody binding where an antibody X binds to target Y less strongly and/or with a larger dissociation constant than to target Z, and in this context antibody X has a lesser affinity for target Y than for Z. The affinity of binding between an antibody and its target antigen, can be expressed as KA equal to $1/K_D$ where $K_D$ is equal to $k_{on}/k_{off}$. The $k_{on}$ and $k_{off}$ values can be measured using surface plasmon resonance technology, for example, using a Molecular Affinity Screening System (MASS-1) (Sierra Sensors GmbH, Hamburg, Germany). An antagonist or blocking antibody is an antibody that partially or fully blocks inhibits or neutralizes a biological activity related to the target antigen relative to the activity under similar physiological conditions when the antibody is not present. Antagonists can be competitive, non-competitive or irreversible. A competitive antagonist is a substance that binds to a natural ligand or receptor at the same site as the natural ligand-receptor interaction or binds allosterically in a manner that induces a change to prevent normal binding. A non-competitive antagonist binds at a different site than the natural ligand-receptor interaction, but lower the KD or signal resulting from the interaction. An irreversible inhibitor causes covalent modifications to the receptor preventing any subsequent binding.

As used herein, the term "avidity" refers to the overall stability of the binding complex between the antibody and the target antigen. It is governed by three factors, (i) the intrinsic affinity of the antibody for the antigen, (2) the valency of the antibody, and (3) the geometric arrangement of the interacting components. Affinity is the strength of the interaction between the antibody and a single target, whereas avidity is an accumulated strength of multiple affinities. In one embodiment, the antibodies provided herein are divalent.

As used herein, an antibody "preferentially binds" binds a first antigen relative to a second antigen if it binds the first antigen with greater affinity than it does the second antigen. Preferential binding can be at least any of 2-fold, 5-fold, 9-fold, 10-fold, 20-fold, 30-fold, 40-fold, 50-fold, 100-fold, 500-fold or 1000-fold greater affinity. So, for example, an antibody preferentially binds LRP6 relative to LRP5 if it binds LRP6 with greater affinity than it binds LRP5.

As used herein, an antibody "specifically binds" or is "specific for" a target antigen or target group of antigens if it binds the target antigen or each member of the target group of antigens with an affinity of at least any of $1\times10^{-6}$ M, $1\times10^{-7}$M, $1\times10^{-8}$M, $1\times10^{-9}$ M, $1\times10^{-19}$ M, $1\times10^{-11}$ M, $1\times10^{-12}$ M, and, for example, binds to the target antigen or each member of the target group of antigens with an affinity that is at least two-fold greater than its affinity for non-target antigens to which it is being compared. Typically, specific binding is characterized by binding the antigen with sufficient affinity that the antibody is useful as a diagnostic to detect the antigen or epitope and/or as a therapeutic agent in targeting the antigen or epitope.

As used herein, and antibody "blocks" or "antagonizes" the binding of a ligand to receptor when it competitively reduces or prevents interaction all of the ligand with the receptor. In an embodiment, the measured level of reduction can be at least any of 5%, 10%, 25%, 50%, 80%, 90%, 95%, 97.5%, 99%, 99.5%, 99.9% of a control (e.g. untreated) cell. For example, an antibody that antagonizes or blocks the binding of a Wnt ligand to an LRP6 receptor competitively reduces or prevents the interaction of a Wnt protein with an LRP6 receptor. This results in attenuation or blocking of a downstream signaling event associated with Wnt signaling. This includes, for example, activation of disheveled, dissolution of the beta-catenin destructive complex, lower cytosolic levels of β-catenin, and/or lower activity of TCF/LEF-mediated transcription.

The term "captures" with respect to an antibody target (e.g., antigen, analyte, immune complex), typically indicates that an antibody binds a majority of the antibody targets in a pure population (assuming appropriate molar ratios). For example, an antibody that binds a given antibody target typically binds to at least ⅔ of the antibody targets in a solution (e.g., at least any of 67, 75, 80, 85, 90, 91, 92, 93, 94, 95, 96, 97, 98, 99, or 100%). One of skill will recognize that some variability will arise depending on the method and/or threshold of determining binding.

The term "conjugate" refers to a first molecule, e.g., an antibody (an "immunoconjugate"), chemically coupled with a moiety, such as a detectable label or a biologically active moiety, such as a drug, toxin or chemotherapeutic or cytotoxic agent. Accordingly, this disclosure contemplates antibodies conjugated with one or more moieties. Furthermore, an antibody can be "conjugated antibody" or a "non-conjugated antibody" (that is, not conjugated with a moiety.

As used herein, the term "antibody-drug conjugate" or ("ADC") refers to an antibody conjugated with a drug. Typically, conjugation involves covalent binding through a linker.

As used herein, the term "labeled" molecule (e.g., nucleic acid, protein, or antibody) refers to a molecule that is bound to a detectable label, either covalently, through a linker or a chemical bond, or noncovalently, through ionic, van der Waals, electrostatic, or hydrogen bonds, such that the presence of the molecule may be detected by detecting presence of the detectable label bound to the molecule.

As used herein, the term "detectable label" refers to a composition detectable by spectroscopic, photochemical, biochemical, immunochemical, chemical, or other physical means. Examples of detectable labels are described herein and include, without limitation, colorimetric, fluorescent, chemiluminescent, enzymatic, and radioactive labels. For the purposes of the present disclosure, a detectable label can also be a moiety that does not itself produce a signal (e.g., biotin), but that binds to a second moiety that is able to produce a signal (e.g., labeled avidin).

The term "cross-linked" with respect to an antibody refers to attachment of the antibody to a solid or semisolid matrix (e.g., sepharose, beads, microtiter plate), or to another protein or antibody. For example, an antibody can be multimerized to create an antibody complex with multiple (more than 2) antigen-binding sites. The antibody can be multimerized by expressing the antibody as a high-valency isotype (e.g., IgA or IgM, which typically form complexes of 2 or 5 antibodies, respectively). Antibody multimerization can also be carried out by using a cross-linker comprising a reactive group capable of linking proteins (e.g., carbodiimide, NHS esters, etc.). Methods and compositions for cross-linking an antibody to a matrix are described, e.g., in the Abcam and New England Biolab catalogs and websites (available at abcam.com and neb.com). Cross-linker compounds with various reactive groups are described, e.g., in Thermo Fisher Scientific catalog and website (available at piercenet.com).

As used herein, the term "immunoassay" refers to a method for detecting an analyte by detecting binding between an antibody that recognizes the analyte and the analyte.

As used herein, the term "expression construct" refers to a polynucleotide comprising an expression control sequence operatively linked with a heterologous nucleotide sequence (i.e., a sequence to which the expression control sequence is not normally connected to in nature) that is to be the subject of expression. As used herein, the term "expression vector" refers to a polynucleotide comprising an expression construct and sequences sufficient for replication in a host cell or insertion into a host chromosome.

Plasmids and viruses are examples of expression vectors. As used herein, the term "expression control sequence" refers to a nucleotide sequence that regulates transcription and/or translation of a nucleotide sequence operatively linked thereto. Expression control sequences include promoters, enhancers, repressors (transcription regulatory sequences) and ribosome binding sites (translation regulatory sequences).

The term "vector" as used herein comprises any intermediary vehicle for a nucleic acid molecule which enables said nucleic acid molecule, for example, to be introduced into prokaryotic and/or eukaryotic cells and/or integrated into a genome, and include plasmids, phagemids, bacteriophages or viral vectors such as retroviral based vectors, Adeno Associated viral vectors and the like. The term "plasmid" as used herein generally refers to a construct of extrachromosomal genetic material, usually a circular DNA duplex, which can replicate independently of chromosomal DNA.

As used herein, a nucleotide sequence is "operatively linked" with an expression control sequence when the expression control sequence functions in a cell to regulate transcription of the nucleotide sequence. This includes promoting transcription of the nucleotide sequence through an interaction between a polymerase and a promoter.

As used herein, a "host cell" refers to a recombinant cell comprising an expression construct.

As used herein, the term "biological sample" refers to a sample containing cells (e.g., tumor cells) or biological molecules derived from cells. A biological sample can be obtained from a subject, e.g., a patient, from an animal, such as an animal model, or from cultured cells, e.g., a cell line or cells removed from a patient and grown in culture for observation. A biological sample can comprise tissue and/or liquid. It can be obtained from any biological source including without limitation blood, a blood fraction (e.g., serum or plasma), cerebrospinal fluid (CSF), lymph, tears, saliva, sputum, buccal swab, milk, urine or feces. A biological sample can be a biopsy, such as a tissue biopsy, such as needle biopsy, fine needle biopsy, surgical biopsy, etc. The sample can comprise a tissue sample harboring a lesion or suspected lesion, although the biological sample may also be derived from another site, e.g., a site of suspected metastasis, a lymph node, or from the blood. A biological sample can be a fraction of a sample taken from a subject. An example of a tissue sample includes a brain tissue sample or a nerve tissue sample. Methods of obtaining such biological samples are known in the art including but not limited to standard blood retrieval procedures.

As used herein, the term "diagnosis" refers to a relative probability that a subject has a disorder such as cancer. Similarly, the term "prognosis" refers to a relative probability that a certain future outcome may occur in the subject. For example, in the context of the present disclosure, prognosis can refer to the likelihood that an individual will develop cancer, have recurrence, that the cancer will metastasize, that the cancer will be cured, or the likely severity of the disease (e.g., severity of symptoms, rate of functional decline, survival, etc.). The terms are not intended to be absolute, as will be appreciated by any one of skill in the field of medical diagnostics.

As used herein, the term terms "therapy," "treatment," "therapeutic intervention" and "amelioration" refer to any activity resulting in a reduction in the severity of symptoms. In the case of cancer, treatment can refer to, e.g., reducing tumor size, number of cancer cells, growth rate, metastatic activity, reducing cell death of non-cancer cells, reduced nausea and other chemotherapy or radiotherapy side effects, etc. The terms "treat" and "prevent" are not intended to be absolute terms. Treatment and prevention can refer to any delay in onset, amelioration of symptoms, improvement in patient survival, increase in survival time or rate, etc. Treatment and prevention can be complete (undetectable levels of neoplastic cells) or partial, such that fewer neoplastic cells are found in a patient than would have occurred without the present intervention. The effect of treatment can be compared to an individual or pool of individuals not receiving the treatment, or to the same patient prior to treatment or at a different time during treatment. In some aspects, the severity of disease is reduced by at least 10%, as compared, e.g., to the individual before administration or to a control individual not undergoing treatment. In some aspects, the severity of disease is reduced by at least 25%, 50%, 75%, 80%, or 90%, or in some cases, no longer detectable using standard diagnostic techniques.

As used herein, the terms "effective amount," "effective dose," and "therapeutically effective amount," refer to an amount of an agent, such as an antibody or immunoconjugate, that is sufficient to generate a desired response, such as reduce or eliminate a sign or symptom of a condition or ameliorate a disorder. In some examples, an "effective amount" is one that treats (including prophylaxis) one or more symptoms and/or underlying causes of any of a disorder or disease and/or prevents progression of a disease. For example, for the given parameter, a therapeutically effective amount will show an increase or decrease of therapeutic effect at least any of 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least any of a 1.2-fold, 1.5-fold, 2-fold, 5-fold, or more effect over a control.

As used herein, the term "pharmaceutical composition" refers to a composition comprising a pharmaceutical compound (e.g., a drug) and a pharmaceutically acceptable carrier.

As used herein, the term "pharmaceutically acceptable" refers to a carrier that is compatible with the other ingredients of a pharmaceutical composition and can be safely administered to a subject. The term is used synonymously with "physiologically acceptable" and "pharmacologically acceptable". Pharmaceutical compositions and techniques for their preparation and use are known to those of skill in the art in light of the present disclosure. For a detailed listing of suitable pharmacological compositions and techniques for their administration one may refer to texts such as Remington's Pharmaceutical Sciences, 17th ed. 1985; Brunton et al., "Goodman and Gilman's The Pharmacological Basis of Therapeutics," McGraw-Hill, 2005; University of the Sciences in Philadelphia (eds.), "Remington: The Science and Practice of Pharmacy," Lippincott Williams & Wilkins, 2005; and University of the Sciences in Philadelphia (eds.), "Remington: The Principles of Pharmacy Practice," Lippincott Williams & Wilkins, 2008.

Pharmaceutically acceptable carriers will generally be sterile, at least for human use. A pharmaceutical composition will generally comprise agents for buffering and preservation in storage, and can include buffers and carriers for appropriate delivery, depending on the route of administration. Examples of pharmaceutically acceptable carriers include, without limitation, normal (0.9%) saline, phosphate-buffered saline (PBS) Hank's balanced salt solution (HBSS) and multiple electrolyte solutions such as Plasma-Lyte ATM (Baxter).

Acceptable carriers, excipients and/or stabilizers are non-toxic to recipients at the dosages and concentrations employed, and include buffers such as phosphate, citrate, and other organic acids; antioxidants including ascorbic acid, glutathione, cysteine, methionine and citric acid; preservatives (such as ethanol, benzyl alcohol, phenol, m-cresol, p-chlor-m-cresol, methyl or propyl parabens, benzalkonium chloride, or combinations thereof); amino acids such as arginine, glycine, ornithine, lysine, histidine, glutamic acid, aspartic acid, isoleucine, leucine, alanine, phenylalanine, tyrosine, tryptophan, methionine, serine, proline and combinations thereof; monosaccharides, disaccharides and other carbohydrates; low molecular weight (less than about 10 residues) polypeptides; proteins, such as gelatin or serum albumin; chelating agents such as EDTA; sugars such as trehalose, sucrose, lactose, glucose, mannose, maltose, galactose, fructose, sorbose, raffinose, glucosamine, N-methylglucosamine, galactosamine, and neuraminic acid; and/or non-ionic surfactants such as Tween, Pluronics, Triton-X, or polyethylene glycol (PEG).

The terms "dose" and "dosage" are used interchangeably herein. A dose refers to the amount of active ingredient given to an individual at each administration. For the present invention, the dose can refer to the concentration of the antibody or associated components, e.g., the amount of therapeutic agent or dosage of radiolabel. The dose will vary depending on a number of factors, including frequency of administration; size and tolerance of the individual; severity of the condition; risk of side effects; the route of administration; and the imaging modality of the detectable label (if present). One of skill in the art will recognize that the dose can be modified depending on the above factors or based on therapeutic progress. The term "dosage form" refers to the particular format of the pharmaceutical, and depends on the route of administration. For example, a dosage form can be in a liquid, e.g., a saline solution for injection.

As used herein, the term "subject" refers to an individual animal. The term "patient" as used herein refers to a subject under the care or supervision of a health care provider such as a doctor or nurse. Subjects include mammals, such as humans and non-human primates, such as monkeys, as well as dogs, cats, horses, bovines, rabbits, rats, mice, goats, pigs, and other mammalian species. Subjects can also include avians. A patient can be an individual that is seeking treatment, monitoring, adjustment or modification of an existing therapeutic regimen, etc. The term "cancer subject" refers to an individual that has been diagnosed with cancer. Cancer patients can include individuals that have not received treatment, are currently receiving treatment, have had surgery, and those that have discontinued treatment.

In the context of treating cancer, a subject in need of treatment can refer to an individual that has cancer or a pre-cancerous condition, has had cancer and is at risk of recurrence, is suspected of having cancer, is undergoing standard treatment for cancer, such as radiotherapy or chemotherapy, etc.

"Cancer", "tumor," "transformed" and like terms include precancerous, neoplastic, transformed, and cancerous cells, and can refer to a solid tumor, or a non-solid cancer (see, e.g., Edge et al. AJCC Cancer Staging Manual (7th ed. 2009); Cibas and Ducatman Cytology: Diagnostic principles and clinical correlates (3rd ed. 2009)). Cancer includes both benign and malignant neoplasms (abnormal growth). "Transformation" refers to spontaneous or induced phenotypic changes, e.g., immortalization of cells, morphological changes, aberrant cell growth, reduced contact inhibition and anchorage, and/or malignancy (see, Freshney, Culture of Animal Cells a Manual of Basic Technique (3rd ed. 1994)). Although transformation can arise from infection with a transforming virus and incorporation of new genomic DNA, or uptake of exogenous DNA, it can also arise spontaneously or following exposure to a carcinogen.

The term "cancer" can refer to any cancer, including without limitation, leukemias, carcinomas, sarcomas, adenocarcinomas, lymphomas, solid and lymphoid cancers, etc. Examples of different types of cancer include, but are not limited to, lung cancer (e.g., non-small cell lung cancer or NSCLC), breast cancer, prostate cancer, colorectal cancer, bladder cancer, ovarian cancer, leukemia, liver cancer (i.e., hepatocarcinoma), renal cancer (i.e., renal cell carcinoma), thyroid cancer, pancreatic cancer, uterine cancer, cervical cancer, testicular cancer, esophageal cancer, stomach (gastric) cancer, kidney cancer, cancer of the central nervous system, skin cancer, glioblastoma and melanoma.

As used herein, a chemical entity, such as a polypeptide, is "substantially pure" if it is the predominant chemical entity of its kind (e.g., of polypeptides) in a composition. This includes the chemical entity representing more than 50%, more than 80%, more than 90%, more than 95%, more than 98%, more than 99%, more than 99.5%, more than 99.9%, or more than 99.99% of the chemical entities of its kind in the composition.

The phrase "isolated antibody" refers to antibody produced in vivo or in vitro that has been removed from the source that produced the antibody, for example, an animal, hybridoma or other cell line (such as recombinant insect, yeast or bacterial cells that produce antibody).

"Substantially pure" or "isolated" means an object species is the predominant species present (i.e., on a molar basis, more abundant than any other individual macromolecular species in the composition), and a substantially purified fraction is a composition wherein the object species comprises at least about 50% (on a molar basis) of all macromolecular species present. Generally, a substantially pure composition means that about 80% to 90% or more of the macromolecular species present in the composition is the purified species of interest. The object species is purified to essential homogeneity (contaminant species cannot be detected in the composition by conventional detection methods) if the composition consists essentially of a single macromolecular species. Solvent species, small molecules (<500 Daltons), stabilizers (e.g., BSA), and elemental ion species are not considered macromolecular species for purposes of this definition.

The term "sequence identity" as used herein refers to the percentage of sequence identity between two polypeptide sequences or two nucleic acid sequences. To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions.times.100%). In one embodiment, the two sequences are the same length. The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules of the present application. BLAST protein searches can be performed with the XBLAST program parameters set, e.g., to score-50, wordlength=3 to obtain amino acid sequences homologous to a protein molecule described herein. To obtain gapped alignments for comparison purposes, Gapped BLAST can be utilized as described in Altschul et al., 1997, Nucleic Acids Res. 25:3389-3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used (see, e.g., the NCBI website). Another preferred, non-limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

For antibodies, percentage sequence identities can be determined when antibody sequences maximally aligned by IMGT. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, multiplied by 100 to convert to percentage.

Percent amino acid sequence identity may also be determined using the sequence comparison program NCBI-BLAST2 (Altschul et al., Nucleic Acids Res. 25:3389-3402 (1997)). The NCBI-BLAST2 sequence comparison program may be obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program NCBI-BLAST2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. The term "nucleic acid sequence" as used herein refers to a sequence of nucleoside or nucleotide monomers consisting of naturally occurring bases, sugars and intersugar (backbone) linkages and includes cDNA. The term also includes modified or substituted sequences comprising non-naturally occurring monomers or portions thereof. The nucleic acid sequences of the present application may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine. It is understood that polynucleotides comprising non-transcribable nucleotide bases may be useful as probes in, for example, hybridization assays. The nucleic acid can be either double stranded or single stranded, and represents the sense or antisense strand. Further, the term "nucleic acid" includes the complementary nucleic acid sequences as well as codon optimized or synonymous codon equivalents.

The term "isolated nucleic acid" as used herein refers to a nucleic acid substantially free of cellular material or culture medium when produced by recombinant DNA techniques, or chemical precursors, or other chemicals when chemically synthesized. An isolated nucleic acid is also substantially free of sequences that naturally flank the nucleic acid (i.e. sequences located at the 5' and 3' ends of the nucleic acid) from which the nucleic acid is derived.

By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature (Tm=81.5° C.−16.6 (Log 10 [Na+])+0.41(% (G+C)−600/I), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example, if nucleic acid molecules are sought that have a >95% identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5× sodium chloride/sodium citrate (SSC)/5×Denhardt's solution/1.0% SDS at Tm−5° C. based on the above equation, followed by a wash of 0.2×SSC/0.1% SDS at 60° C. Moderately stringent hybridization conditions include a washing step in 3×SSC at 42° C. It is understood, however, that equivalent stringencies may be achieved using alternative buffers, salts and temperatures. Additional guidance regarding hybridization conditions may be found in: Current Protocols in Molecular Biology, John Wiley & Sons, N.Y., 2002, and in: Sambrook et al., Molecular Cloning: A Laboratory Manual, Cold Spring Harbor Laboratory Press, 2001.

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. "Treating" and "Treatment" can also mean prolonging survival as compared to expected survival if not receiving treatment. "Treating" and "treatment" as used herein also include prophylactic treatment. For example, a subject with cancer can be treated to prevent progression can be treated with an antibody, immunoconjugate, nucleic acid or composition described herein to prevent progression.

As used herein, the term "administration" means to provide or give a subject an agent, such as a composition comprising an effective amount of an antibody by an effective route such as an intratumor or an intravenous administration route.

As used herein, the term "diluent" refers to a pharmaceutically acceptable carrier which does not inhibit a physiological activity or property of an active compound, such as an antibody, or immunoconjugate, to be administered and does not irritate the subject and does not abrogate the biological activity and properties of the administered compound. Diluents include any and all solvents, dispersion media, coatings, surfactants, antioxidants, preservative salts, preservatives, binders, excipients, disintegration agents, lubricants, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

Compositions or methods "comprising" or "including" one or more recited elements may include other elements not specifically recited. For example, a composition that "comprises" or "includes" an antibody may contain the antibody alone or in combination with other ingredients.

In understanding the scope of the present disclosure, the term "consisting" and its derivatives, as used herein, are intended to be close ended terms that specify the presence of stated features, elements, components, groups, integers, and/or steps, and also exclude the presence of other unstated features, elements, components, groups, integers and/or steps.

The recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about." Further, it is to be understood that the singular forms of the articles "a," "an," and "the" include plural references unless the context clearly dictates otherwise. For example, the term "an antibody" or "at least one antibody" can include a plurality of antibodies, including mixtures thereof.

The terms "Frizzled" and "FZD" refer, depending on context, to any gene or protein member of the Frizzled family. Frizzled proteins are involved in the activation of Disheveled protein in the cytosol. Frizzled refers to any of Frizzled-1, Frizzled-2, Frizzled-3, Frizzled-4, Frizzled-5, Frizzled-6, Frizzled-7, Frizzled-8, Frizzled-9 and Frizzled-10.

"Lipoprotein receptor-related proteins", "low density lipoprotein receptor-related proteins" (HGNC) or "prolow-density lipoprotein receptor-related protein" (UniProt), abbreviated "LRP", are a group of genes and proteins. They include: LRP1, LRP1B, LRP2 (megalin), LRP3, LRP4, LRP5, LRP6, LRP8 (apolipoprotein e receptor), LRP10, LRP11, and LRP12. LRP5 and LRP6 are part of the LRP5/LRP6/Frizzled co-receptor group that is involved in canonical Wnt pathway. LRP5 is also known as LRP5, BMND1, EVR1, EVR4, HBM, LR3, LRP-5, LRP7, OPPG, OPS, OPTA1, VBCH2, and LDL receptor related protein 5. The LRP5 gene has ENTREZ Gene ID: 4041 and the protein has NCBI Reference Sequence: NP_002326. The LRP6 gene has ENTREZ Gene ID: 4040 and the protein has NCBI Reference Sequence: NP_002327. LRP6 is also known as ADCAD2, STHAG7.

II. Disorders Associated with LRP Signaling Dysregulation

Wnt binding to LRP5 or LRP6 destabilizes a beta-catenin binding complex causing beta-catenin degradation. The result is increased levels of intracellular beta-catenin. Accordingly, provided herein are methods of blocking Wnt binding to LRP family proteins such as LRP5 or LRP6.

An "LRP-associated disorder" (e.g., an "LRP5-associated disorder" or an "LRP6-associated disorder") refers to a condition or disease correlated with dysregulation of the particular LRP receptor referred to. Dysregulation refers to abnormal decreases or increases in signaling that affect normal beta-catenin mediated transcriptional changes or any other intracellular signaling pathways governed by these receptors. So, for example, abnormal LRP-associated increases in signaling, e.g., through the canonical Wnt signaling pathway (Wnt3/Wnt3A), are associated with certain cancers and with increases in bone density, while abnormal LRP-associated decreases in signaling are associated with decreases in bone density.

Antibodies that block the binding of Wnt to LRP5 or LRP6 are useful in the treatment of cancer. In particular, method of blocking Wnt binding to LRP6 is useful in the treatment of brain cancer, breast cancer, colon cancer, endometrial cancer, esophageal cancer, kidney cancer, liver cancer, lung cancer, ovarian cancer, skin cancer, stomach cancer and testicular cancer.

III. Anti-LRP Antibodies

A. Antibodies

LRP5 and LRP6 each have two Wnt binding sites. The majority of Wnt activators of β-catenin signaling, including Wnt 1, 2, 2b, 6, 8a, 9a, 9b, 10b etc., associate with β propeller 1 and 2 regions of LRP5 and LRP6. This site is referred to herein as the "non-Wnt3a binding site". Wnt proteins Wnt3 and Wnt3a are known to associate with a distinct site on β propeller regions 3 and 4 of LRP5 and LRP6. This site is referred to herein as the "Wnt3a binding site". Antibody binding to LRP5 or LRP6 that blocks binding of Wnt ligands to a particular binding site decreases activity of the signaling pathway associated with Wnt ligand binding to that site. Such blocking activity also may, in certain circumstances, potentiate activity of the signaling pathway associated with Wnt ligand binding to the other binding site. So, for example, an antibody that blocks binding of a Wnt ligand to the Wnt3a binding site inhibits activity of the Wnt3a signaling pathway and may potentiate activity of the non-Wnt3a signaling pathway. Similarly, an antibody that blocks binding of a Wnt ligand to the non-Wnt3a binding site inhibits activity of the non-Wnt3a signaling pathway and may potentiate activity of the Wnt3a signaling pathway.

Antibodies against LRP6 receptors are described herein. Certain of these antibodies block binding of Wnt ligands to the Wnt3a binding site of LRP6. Others of these antibodies block binding of Wnt ligands to the non-Wnt3a binding site. These antibodies block ligand Wnt binding and modulate activity of the Wnt signaling pathway. These antibodies also have anti-proliferative effects have therapeutic potential for treating cancer and other diseases where the LRP receptors are dysregulated.

Accordingly, an aspect of the disclosure includes an isolated antibody that specifically binds LRP6 receptor. The antibodies comprise a light chain variable region and a heavy chain variable region, the heavy chain variable region comprising complementarity determining regions CDR-H1, CDR-H2 and CDR-H3, the light chain variable region comprising complementarity determining region CDR-L1, CDR-L2 and CDR-L3, and with the amino acid sequences of said CDRs comprising, consisting essentially of, or consisting of sequences selected from sequences in Table 1 or 2.

In an embodiment, the antibody comprises a CDR sequence set selected from the CDR sequence sets in Table 1, that is, for clones LRP6-A1, LRP6-A10, LRP6-B6, LRP6-E3, LRP6-G3, LRP6-G9.

Also described herein are heavy chain and light chain variable regions. Table 2 provides exemplary variable domain sequences for the Fab heavy and light chains, from clones LRP6-A1, LRP6-A10, LRP6-B6, LRP6-E3, LRP6-G3, LRP6-G9. Antibodies comprising the sequences in Table 2 or sequences substantially identical thereto, wherein the CDRs are a CDR sequence set identified in Tables 1 are also contemplated. In another embodiment, the antibody comprises a heavy chain variable region comprising: i) a heavy chain amino acid sequence as set forth in Table 2; ii) an amino acid sequence with at least 50%, at least 60%, at least 70%, at least 80%, at least 90%, at least 95%, at least 98% or at least 99% sequence identity to the heavy chain amino acid sequence as set forth in Table 2, wherein the CDR sequences are a CDR sequence set as set forth in Table 1, or iii) a conservatively substituted amino acid sequence of i) wherein the CDR sequences are a CDR sequence set as set forth in Table 1.

In another embodiment, the antibody comprises a light chain variable region comprising i) a light chain amino acid sequence as set forth in Table 2, ii) an amino acid sequence with at least 50%, at least 60%, at least 70%, at least 80%, at least 90%, at least 95%, at least 98% or at least 99% sequence identity to the light chain amino acid sequence as set forth in Table 2, wherein the CDR sequences are a CDR sequence set as set forth in Table 1, or iii) a conservatively substituted amino acid sequence of i) wherein the CDR sequences are a CDR sequence set as set forth in Table 1.

Antibodies LRP6-A1, LRP6-A10, LRP6-B6, LRP6-E3, LRP6-G3, LRP6-G9 specifically bind LRP6 and inhibit Wnt ligand-induced signaling. Antibodies LRP6-A10 and LRP6-B6 significantly inhibit Wnt3a-induced activity, presumably by blocking binding of Wnt ligands to the Wnt3a binding site, thus blocking TCF/LEF mediated transcription in response to Wnt3a conditioned media (CM). Antibodies LRP6-A1, LRP6-G3 and LRP6-G9 inhibit non-Wnt3a-induced activity, presumably by blocking binding of Wnt ligands to the non-Wnt3a binding site. Furthermore, antibodies LRP6-G3 and LRP6-G9 significantly potentiate the Wnt3a-induced activity.

Amino acid sequences for CDRs of these antibodies are provided in Table 1.

TABLE 1

| | | | CDR sequences of anti-LRP6 antibodies | | | | |
|---|---|---|---|---|---|---|---|
| | CDLR-L1 | CDR-L2 | CDR-L3 | CDR-H1 | CDR-H2 | CDR-H3 | Epitope Group |
| LRP6-A1 | SVSSA (SEQ ID NO: 14) | SASSLYS (SEQ ID NO: 15) | YYWPI (SEQ ID NO: 20) | LSYYYI (SEQ ID NO: 2) | SIYSSYGYTS (SEQ ID NO: 6) | TVRGSKKPYFSGWAM (SEQ ID NO: 10) | 1 |
| LRP6-A10 | SVSSA (SEQ ID NO: 14) | SASSLYS (SEQ ID NO: 15) | YSWGPF (SEQ ID NO: 17) | ISYSSI (SEQ ID NO: 25) | YISSYYGYTY (SEQ ID NO: 7) | AHYFPWAGAM (SEQ ID NO: 11) | 2 |
| LRP6-B6 | SVSSA (SEQ ID NO: 14) | SASSLYS (SEQ ID NO: 15) | YYFLI (SEQ ID NO: 18) | ISYSSI (SEQ ID NO: 25) | SISPYYGYTY (SEQ ID NO: 8) | SSYFPWFSAM (SEQ ID NO: 12) | 2 |
| LRP6-E3 | SVSSA (SEQ ID NO: 14) | SASSLYS (SEQ ID NO: 15) | AGSAPYHLI (SEQ ID NO: 19) | LYYYSM (SEQ ID NO: 4) | SIYSSYGYTY (SEQ ID NO: 9) | YAGYYYYPWAY YGWPFSGL (SEQ ID NO: 13) | 1 |
| LRP6-G3 | SVSSA (SEQ ID NO: 14) | SASSLYS (SEQ ID NO: 15) | YYWPI (SEQ ID NO: 20) | ISSYYI (SEQ ID NO: 5) | SIYSSYGYTS (SEQ ID NO: 6) | TVRGSKKPYFSGWAM (SEQ ID NO: 10) | 1 |
| LRP6-G9 | SVSSA (SEQ ID NO: 14) | SASSLYS (SEQ ID NO: 15) | YYWPI (SEQ ID NO: 20) | IYSYYI (SEQ ID NO: 26) | SIYSSYSYTS (SEQ ID NO: 27) | TVRGSKKPYFSGWAM (SEQ ID NO: 10) | 1 |

Amino acid and nucleotide sequences for the variable heavy and variable light domains are provided in Table 2:

TABLE 2

| heavy chain and light chain DNA and amino acid sequences of LRP6-A1, LRP6-A10, LRP6-B6, LRP6-E3, LRP6-G3, LRP6-G9. |
|---|

LRP6-A1:
VH-DNA:
(SEQ ID NO: 28)
GAGGTTCAGCTGGTGGAGTCTGGCGGTGGCCTGGTGCAGCCAGGGGGCTC

ACTCCGTTTGTCCTGTGCAGCTTCTGGCTTCAACCTCTCTTATTATTATATCCACTGGGT

GCGTCAGGCCCCGGGTAAGGGCCTGGAATGGGTTGCATCTATTTATTCTTCTTATGGCT

ATACTTCTTATGCCGATAGCGTCAAGGGCCGTTTCACTATAAGCGCAGACACATCCAAA

AACACAGCCTACCTACAAATGAACAGCTTAAGAGCTGAGGACACTGCCGTCTATTATTG

TGCTCGCACTGTTCGTGGATCCAAAAAACCGTACTTCTCTGGTTGGGCTATGGACTACT

GGGGTCAAGGAACCCTGGTCACCGTCTCCTCG

VH-AA
(SEQ ID NO: 29)
EVQLVESGGGLVQPGGSLRLSCAASGFNLSYYYIHWVRQAPGKGLEWVASIYS

SYGYTSYADSVKGRFTISADTSKNTAYLQMNSLRAEDTAVYYCARTVRGSKKPYFSGWAM

DYWGQGTLVTVSS

VL-DNA
(SEQ ID NO: 30)
GATATCCAGATGACCCAGTCCCCGAGCTCCCTGTCCGCCTCTGTGGGCGAT

AGGGTCACCATCACCTGCCGTGCCAGTCAGTCCGTGTCCAGCGCTGTAGCCTGGTATC

AACAGAAACCAGGAAAAGCTCCGAAGCTTCTGATTTACTCGGCATCCAGCCTCTACTCT

GGAGTCCCTTCTCGCTTCTCTGGTAGCCGTTCCGGGACGGATTTCACTCTGACCATCA

GCAGTCTGCAGCCGGAAGACTTCGCAACTTATTACTGTCAGCAATACTACTGGCCGATC

ACGTTCGGACAGGGTACCAAGGTGGAGATCAAACGT

VL-AA
(SEQ ID NO: 31)
DIQMTQSPSSLSASVGDRVTITCRASQSVSSAVAWYQQKPGKAPKLLIYSASSL

YSGVPSRFSGSRSGTDFTLTISSLQPEDFATYYCQQYYWPITFGQGTKVEIKR

LRP6-A10
VH-DNA
(SEQ ID NO: 32)
GAGGTTCAGCTGGTGGAGTCTGGCGGTGGCCTGGTGCAGCCAGGGGGCTC

ACTCCGTTTGTCCTGTGCAGCTTCTGGCTTCAACATCTCTTATTCTTCTATCCACTGGGT

GCGTCAGGCCCCGGGTAAGGGCCTGGAATGGGTTGCATATATTTCTTCTTATTATGGCT

ATACTTATTATGCCGATAGCGTCAAGGGCCGTTTCACTATAAGCGCAGACACATCCAAA

AACACAGCCTACCTACAAATGAACAGCTTAAGAGCTGAGGACACTGCCGTCTATTATTG

TGCTCGCGCTCATTACTTCCCGTGGGCTGGTGCTATGGACTACTGGGGTCAAGGAACC

CTGGTCACCGTCTCCTCG

VH-AA
(SEQ ID NO: 33)
EVQLVESGGGLVQPGGSLRLSCAASGFNISYSSIHWVRQAPGKGLEWVAYISS

YYGYTYYADSVKGRFTISADTSKNTAYLQMNSLRAEDTAVYYCARAHYFPWAGAMDYWG

QGTLVTVSS

TABLE 2-continued heavy chain and light chain DNA and amino acid sequences
of LRP6-A1, LRP6-A10, LRP6-B6, LRP6-E3, LRP6-G3, LRP6-G9.

VL-DNA
                                              (SEQ ID NO: 34)
GATATCCAGATGACCCAGTCCCCGAGCTCCCTGTCCGCCTCTGTGGGCGAT

AGGGTCACCATCACCTGCCGTGCCAGTCAGTCCGTGTCCAGCGCTGTAGCCTGGTATC

AACAGAAACCAGGAAAAGCTCCGAAGCTTCTGATTTACTCGGCATCCAGCCTCTACTCT

GGAGTCCCTTCTCGCTTCTCTGGTAGCCGTTCCGGGACGGATTTCACTCTGACCATCA

GCAGTCTGCAGCCGGAAGACTTCGCAACTTATTACTGTCAGCAATACTCTTGGGGTCC

GTTCACGTTCGGACAGGGTACCAAGGTGGAGATCAAACGT

VL-AA
                                              (SEQ ID NO: 35)
DIQMTQSPSSLSASVGDRVTITCRASQSVSSAVAWYQQKPGKAPKLLIYSASSL

YSGVPSRFSGSRSGTDFTLTISSLQPEDFATYYCQQYSWGPFTFGQGTKVEIKR

LRP6-B6
VH-DNA
                                              (SEQ ID NO: 36)
GAGGTTCAGCTGGTGGAGTCTGGCGGTGGCCTGGTGCAGCCAGGGGGCTC

ACTCCGTTTGTCCTGTGCAGCTTCTGGCTTCAACATCTCTTATTCTTCTATCCACTGGGT

GCGTCAGGCCCCGGGTAAGGGCCTGGAATGGGTTGCATCTATTTCTCCTTATTATGGC

TATACTTATTATGCCGATAGCGTCAAGGGCCGTTTCACTATAAGCGCAGACACATCCAA

AAACACAGCCTACCTACAAATGAACAGCTTAAGAGCTGAGGACACTGCCGTCTATTATT

GTGCTCGCTCTTCTTACTTCCCGTGGTTCTCTGCTATGGACTACTGGGGTCAAGGAACC

CTGGTCACCGTCTCCTCG

VH-AA
                                              (SEQ ID NO: 37)
EVQLVESGGGLVQPGGSLRLSCAASGFNISYSSIHWVRQAPGKGLEWVASISP

YYGYTYYADSVKGRFTISADTSKNTAYLQMNSLRAEDTAVYYCARSSYFPWFSAMDYWGQ

GTLVTVSS

VL-DNA
                                              (SEQ ID NO: 38)
GATATCCAGATGACCCAGTCCCCGAGCTCCCTGTCCGCCTCTGTGGGCGAT

AGGGTCACCATCACCTGCCGTGCCAGTCAGTCCGTGTCCAGCGCTGTAGCCTGGTATC

AACAGAAACCAGGAAAAGCTCCGAAGCTTCTGATTTACTCGGCATCCAGCCTCTACTCT

GGAGTCCCTTCTCGCTTCTCTGGTAGCCGTTCCGGGACGGATTTCACTCTGACCATCA

GCAGTCTGCAGCCGGAAGACTTCGCAACTTATTACTGTCAGCAATACTACTTCCTGATC

ACGTTCGGACAGGGTACCAAGGTGGAGATCAAACGT

VL-AA
                                              (SEQ ID NO: 39)
DIQMTQSPSSLSASVGDRVTITCRASQSVSSAVAWYQQKPGKAPKLLIYSASSL

YSGVPSRFSGSRSGTDFTLTISSLQPEDFATYYCQQYYFLITFGQGTKVEIKR

LRP6-E3
VH-DNA
                                              (SEQ ID NO: 40)
GAGGTTCAGCTGGTGGAGTCTGGCGGTGGCCTGGTGCAGCCAGGGGGCTC

ACTCCGTTTGTCCTGTGCAGCTTCTGGCTTCAACCTCTATTATTATTCTATGCACTGGGT

GCGTCAGGCCCCGGGTAAGGGCCTGGAATGGGTTGCATCTATTTATTCTTCTTATGGCT

ATACTTATTATGCCGATAGCGTCAAGGGCCGTTTCACTATAAGCGCAGACACATCCAAA

TABLE 2-continued heavy chain and light chain DNA and amino acid sequences
of LRP6-A1, LRP6-A10, LRP6-B6, LRP6-E3, LRP6-G3, LRP6-G9.

AACACAGCCTACCTACAAATGAACAGCTTAAGAGCTGAGGACACTGCCGTCTATTATTG

TGCTCGCTACGCTGGTTACTACTACTACCCGTGGGCTTACTACGGTTGGCCGTTCTCTG

GTTTGGACTACTGGGGTCAAGGAACCCTGGTCACCGTCTCCTCG

VH-AA
(SEQ ID NO: 41)
EVQLVESGGGLVQPGGSLRLSCAASGFNLYYYSMHWVRQAPGKGLEWVASIY

SSYGYTYYADSVKGRFTISADTSKNTAYLQMNSLRAEDTAVYYCARYAGYYYYPWAYYGW

PFSGLDYWGQGTLVTVSS

VL-DNA
(SEQ ID NO: 42)
GATATCCAGATGACCCAGTCCCCGAGCTCCCTGTCCGCCTCTGTGGGCGAT

AGGGTCACCATCACCTGCCGTGCCAGTCAGTCCGTGTCCAGCGCTGTAGCCTGGTATC

AACAGAAACCAGGAAAAGCTCCGAAGCTTCTGATTTACTCGGCATCCAGCCTCTACTCT

GGAGTCCCTTCTCGCTTCTCTGGTAGCCGTTCCGGGACGGATTTCACTCTGACCATCA

GCAGTCTGCAGCCGGAAGACTTCGCAACTTATTACTGTCAGCAAGCTGGTTCTGCTCC

GTACCATCTGATCACGTTCGGACAGGGTACCAAGGTGGAGATCAAACGT

VL-AA
(SEQ ID NO: 43)
DIQMTQSPSSLSASVGDRVTITCRASQSVSSAVAWYQQKPGKAPKLLIYSASSL

YSGVPSRFSGSRSGTDFTLTISSLQPEDFATYYCQQAGSAPYHLITFGQGTKVEIKR

LRP6-G3
VH-DNA
(SEQ ID NO: 44)
GAGGTTCAGCTGGTGGAGTCTGGCGGTGGCCTGGTGCAGCCAGGGGGCTC

ACTCCGTTTGTCCTGTGCAGCTTCTGGCTTCAACATCTCTTCTTATTATATCCACTGGGT

GCGTCAGGCCCCGGGTAAGGGCCTGGAATGGGTTGCATCTATTTATTCTTCTTATGGCT

ATACTTCTTATGCCGATAGCGTCAAGGGCCGTTTCACTATAAGCGCAGACACATCCAAA

AACACAGCCTACCTACAAATGAACAGCTTAAGAGCTGAGGACACTGCCGTCTATTATTG

TGCTCGCACTGTTCGTGGATCCAAAAAACCGTACTTCTCTGGTTGGGCTATGGACTACT

GGGGTCAAGGAACCCTGGTCACCGTCTCCTCG

VH-AA
(SEQ ID NO: 45)
EVQLVESGGGLVQPGGSLRLSCAASGFNISSYYIHWVRQAPGKGLEWVASIYS

SYGYTSYADSVKGRFTISADTSKNTAYLQMNSLRAEDTAVYYCARTVRGSKKPYFSGWAM

DYWGQGTLVTVSS

VL-DNA
(SEQ ID NO: 30)
GATATCCAGATGACCCAGTCCCCGAGCTCCCTGTCCGCCTCTGTGGGCGAT

AGGGTCACCATCACCTGCCGTGCCAGTCAGTCCGTGTCCAGCGCTGTAGCCTGGTATC

AACAGAAACCAGGAAAAGCTCCGAAGCTTCTGATTTACTCGGCATCCAGCCTCTACTCT

GGAGTCCCTTCTCGCTTCTCTGGTAGCCGTTCCGGGACGGATTTCACTCTGACCATCA

GCAGTCTGCAGCCGGAAGACTTCGCAACTTATTACTGTCAGCAATACTACTGGCCGATC

ACGTTCGGACAGGGTACCAAGGTGGAGATCAAACGT

TABLE 2-continued heavy chain and light chain DNA and amino acid sequences
of LRP6-A1, LRP6-A10, LRP6-B6, LRP6-E3, LRP6-G3, LRP6-G9.

```
VL-AA
                                         (SEQ ID NO: 31)
DIQMTQSPSSLSASVGDRVTITCRASQSVSSAVAWYQQKPGKAPKLLIYSASSL

YSGVPSRFSGSRSGTDFTLTISSLQPEDFATYYCQQYYWPITFGQGTKVEIKR

LRP6-G9
VH-DNA
                                         (SEQ ID NO: 46)
GAGGTTCAGCTGGTGGAGTCTGGCGGTGGCCTGGTGCAGCCAGGGGGCTC

ACTCCGTTTGTCCTGTGCAGCTTCTGGCTTCAACATCTATTCTTATTATATCCACTGGGT

GCGTCAGGCCCCGGGTAAGGGCCTGGAATGGGTTGCATCTATTTATTCTTCTTATAGCT

ATACTTCTTATGCCGATAGCGTCAAGGGCCGTTTCACTATAAGCGCAGACACATCCAAA

AACACAGCCTACCTACAAATGAACAGCTTAAGAGCTGAGGACACTGCCGTCTATTATTG

TGCTCGCACTGTTCGTGGATCCAAAAAACCGTACTTCTCTGGTTGGGCTATGGACTACT

GGGGTCAAGGAACCCTGGTCACCGTCTCCTCG

VH-AA
                                         (SEQ ID NO: 47)
EVQLVESGGGLVQPGGSLRLSCAASGFNIYSYYIHWVRQAPGKGLEWVASIYS

SYSYTSYADSVKGRFTISADTSKNTAYLQMNSLRAEDTAVYYCARTVRGSKKPYFSGWAM

DYWGQGTLVTVSS

VL-DNA
                                         (SEQ ID NO: 30)
GATATCCAGATGACCCAGTCCCCGAGCTCCCTGTCCGCCTCTGTGGGCGAT

AGGGTCACCATCACCTGCCGTGCCAGTCAGTCCGTGTCCAGCGCTGTAGCCTGGTATC

AACAGAAACCAGGAAAAGCTCCGAAGCTTCTGATTTACTCGGCATCCAGCCTCTACTCT

GGGAGTCCCTTCTCGCTTCTCTGGTAGCCGTTCCGGGACGGATTTCACTCTGACCATCA

GCAGTCTGCAGCCGGAAGACTTCGCAACTTATTACTGTCAGCAATACTACTGGCCGATC

ACGTTCGGACAGGGTACCAAGGTGGAGATCAAACGT

VL-AA
                                         (SEQ ID NO: 31)
DIQMTQSPSSLSASVGDRVTITCRASQSVSSAVAWYQQKPGKAPKLLIYSASSL

YSGVPSRFSGSRSGTDFTLTISSLQPEDFATYYCQQYYWPITFGQGTKVEIKR
```

In some embodiments, the variable domain sequences are at least 95%, 96%, 97%, 98%, or 99% similar outside of the CDR regions and the CDR sequence set is 100% identical to the amino acid sequences provided in Table 1.

Also provided in another embodiment, is a competing antibody that competes for binding with an antibody comprising a CDR sequence set described herein. For example, the competing antibody in one embodiment reduces binding of the antibody comprising the CDR sequence set to LRP6 CDR by at least 50%, at least 60%, at least 70%, at least 80% at least 90%, at least 95%, at least 98% or at least 99%.

Also provided in another embodiment, is an antibody that competes with Wnt3a ligand for binding with LRP6, e.g., LRP6-A10 and LRP6-B6.

Also provided in another embodiment, is an antibody that competes with a non-Wnt3a Wnt ligand for binding with LRP6, e.g., LRP6-A1, LRP6-E3, LRP6-G3, LRP6-G9

As demonstrated herein, the antibodies described herein have high affinity for LRP6. For example, the antibodies in one embodiment, have a binding affinity measured by surface plasmon resonance of between about 1 nM and about 50 nM.

The antibody can be a humanized antibody as described herein or a chimeric antibody.

In some embodiments, the antibody is a single chain antibody which can be obtained for example, by fusing the heavy chain and light chain or parts thereof together.

In some embodiments, the antibody is an antibody binding fragment selected from Fab, Fab', F(ab')2, scFv, dsFv, ds-scFv, dimers, nanobodies, minibodies, diabodies, and multimers thereof.

In some other embodiments the antibody is the binding fragment Fab. For some embodiments, the binding fragment is preferable, e.g., in vitro uses.

It may be preferable in other embodiments to have a multivalent antibody or an antibody comprising an Ig portion.

As demonstrated in the Examples, a Fab fragment can be combined with an Ig such as an IgG. In an embodiment, the IgG is IgG1, IgG2, IgG3 or IgG4.

B. Detectably Labeled Antibodies

Detectable labels can include peptide sequences (such a myc tag, HA-tag, V5-tag or NE-tag), fluorescent or luminescent proteins (e.g., green fluorescent protein or luciferase) that can be appended to or introduced into an antibody described herein and which is capable of producing, either directly or indirectly, a detectable signal. For example, the label may be radio-opaque, positron-emitting radionuclide (for example, for use in PET imaging), or a radioisotope, such as $^3$H, $^{13}$N, $^{14}$C, $^{18}$F, $^{32}$P, $^{35}$S, $^{123}$I, $^{125}$I, $^{131}$I; a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; an imaging agent; or a metal ion.

C. Antibody-Drug Conjugates

A further aspect includes an immunoconjugate comprising an antibody described herein and a detectable label or cytotoxic agent.

A chemotherapeutic (anti-cancer) agent can be any agent capable of reducing cancer growth, interfering with cancer cell replication, directly or indirectly killing cancer cells, reducing metastasis, reducing tumor blood supply, etc. Chemotherapeutic agents thus include cytotoxic agents. Cytotoxic agents include but are not limited to saporin, taxanes, *vinca* alkaloids, anthracycline, and platinum-based agents. Classes of chemotherapeutic agents include but are not limited to alkylating agents, antimetabolites, e.g., methotrexate, plant alkaloids, e.g., vincristine, and antitumor antibiotics such as anthracyclines, e.g., doxorubicin as well as miscellaneous drugs that do not fall in to a particular class such as hydroxyurea. Platinum-based drugs, exemplified by cisplatin and oxaliplatin, represent a major class of chemotherapeutics. These drugs bind to DNA and interfere with replication. Taxanes, exemplified by taxol, represent another major class of chemotherapeutics. These compounds act by interfering with cytoskeletal and spindle formation to inhibit cell division, and thereby prevent growth of rapidly dividing cancer cells. Other chemotherapeutic drugs include hormonal therapy. Chemotherapeutics also include agents that inhibit tubulin assembly or polymerization such as maytansine, mertansine, and auristatin. Chemotherapeutic agents also include DNA damage agents such as calicheamicin.

Chemotherapeutic agents can include maytansinoid, auristatin, dolastatin, tubulysin, cryptophycin, pyrrolobenzodiazepine (PBD) dimer, indolinobenzodiazepine dimer, alpha-amanitin, trichothene, SN-38, duocarmycin, CC1065, calicheamincin, an enediyne antibioatic, taxane, doxorubicin derivatives, anthracycline and stereoisomers, azanofide, isosteres, analogs or derivatives thereof.

IV. Nucleic Acids

Further aspects include nucleic acid molecules or polynucleotides, recombinant nucleic acid molecules, expression constructs, and vectors as described herein.

A. Nucleic Acid Molecules

A further aspect includes a nucleic acid molecule as set forth in Table 2, as well as a polynucleotide that hybridizes to one of said sequences, for example, under stringent hybridization conditions. The CDR and variable domain nucleic sequences can be used for example, to prepare expression constructs.

B. Expression Constructs and Vectors

The nucleic acid molecules may be incorporated in a known manner into an appropriate expression construct or expression vector which ensures expression of the protein. Expression constructs can comprise an expression control sequence, e.g., a promoter, operatively linked with a polynucleotide comprising a nucleotide sequence encoding an antibody of this disclosure. Possible expression vectors include but are not limited to cosmids, plasmids, or modified viruses (e.g. replication defective retroviruses, adenoviruses and adeno-associated viruses). The vector should be compatible with the host cell used. The expression vectors are "suitable for transformation of a host cell", which means that the expression vectors contain a nucleic acid molecule encoding the peptides corresponding to epitopes or antibodies described herein.

In an embodiment, the vector is suitable for expressing for example, single chain antibodies by gene therapy. In an embodiment, the vector comprises an IRES and allows for expression of a light chain variable region and a heavy chain variable region. Such vectors can be used to deliver antibody in vivo.

Suitable regulatory sequences may be derived from a variety of sources, including bacterial, fungal, viral, mammalian, or insect genes.

Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

In an embodiment, the regulatory sequences direct or increase expression in neural tissue and/or cells.

The vector can be any vector, including vectors suitable for producing an antibody described herein.

In an embodiment, the vector is a viral vector.

The recombinant expression vectors may also contain a marker gene which facilitates the selection of host cells transformed, infected or transfected with a vector for expressing an antibody or epitope peptide described herein.

The recombinant expression vectors may also contain expression cassettes which encode a fusion moiety (i.e. a "fusion protein") which provides increased expression or stability of the recombinant peptide; increased solubility of the recombinant peptide; and aid in the purification of the target recombinant peptide by acting as a ligand in affinity purification, including for example, tags and labels described herein. Further, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMAL (New England Biolabs, Beverly, MA) and pRIT5 (Pharmacia, Piscataway, NJ) which fuse glutathione S-transferase (GST), maltose E binding protein, or protein A, respectively, to the recombinant protein.

Systems for the transfer of genes both in vitro and in vivo include vectors based on viruses, most notably Herpes Simplex Virus, Adenovirus, Adeno-associated virus (AAV) and retroviruses including lentiviruses. Alternative approaches for gene delivery include the use of naked, plasmid DNA as well as liposome—DNA complexes.

In an aspect the disclosure includes a method for making an antibody described herein, the method comprising synthesizing a nucleic acid molecule that comprises an antibody framework and a CDR sequence set described herein.

V. Recombinant Cells

A further aspect is a recombinant host cell expressing an antibody described herein.

Antibodies as described herein can be made by recombinant expression of nucleic acids encoding the antibody sequences.

Antibodies as disclosed herein can be made by culturing cells engineered to express nucleic acid constructs encoding immunoglobulin polypeptides.

The recombinant host cell can be generated using any cell suitable for producing a polypeptide, for example, suitable for producing an antibody. For example, to introduce a nucleic acid (e.g. a vector) into a cell, the cell may be transfected, transformed or infected, depending upon the vector employed.

Suitable host cells include a wide variety of prokaryotic and eukaryotic host cells. For example, the proteins described herein may be expressed in bacterial cells such as *E. coli*, insect cells (using baculovirus), yeast cells or mammalian cells.

In an embodiment, the cell is a eukaryotic cell selected from a yeast, plant, worm, insect, avian, fish, reptile and mammalian cell.

In another embodiment, the mammalian cell is a CHO cell, a myeloma cell, a spleen cell, or a hybridoma cell.

Yeast and fungi host cells suitable for expressing an antibody include, but are not limited to *Saccharomyces cerevisiae, Schizosaccharomyces pombe*, the genera *Pichia* or *Kluyveromyces* and various species of the genus *Aspergillus*. Examples of vectors for expression in yeast *S. cerevisiae* include pYepSec1, pMFa, pJRY88, and pYES2 (Invitrogen Corporation, San Diego, CA). Protocols for the transformation of yeast and fungi are well known to those of ordinary skill in the art.

Mammalian cells that may be suitable include, among others: COS (e.g., ATCC No. CRL 1650 or 1651), BHK (e.g. ATCC No. CRL 6281), CHO (ATCC No. CCL 61), HeLa (e.g., ATCC No. CCL 2), 293 (ATCC No. 1573) and NS-1 cells. Suitable expression vectors for directing expression in mammalian cells generally include a promoter (e.g., derived from viral material such as polyoma, Adenovirus 2, cytomegalovirus and Simian Virus 40), as well as other transcriptional and translational control sequences. Examples of mammalian expression vectors include pCDM8 and pMT2PC.

VI. Pharmaceutical Compositions

A further aspect is a composition comprising an antibody, immunoconjugate, nucleic acid molecule, vector or recombinant cell described herein, optionally with a suitable diluent, e.g., a pharmaceutically acceptable carrier.

The composition can for example, comprise one or more antibodies or immunoconjugates.

Suitable diluents for polypeptides, including antibodies and/or cells include but are not limited to saline solutions, pH buffered solutions and glycerol solutions or other solutions suitable for freezing polypeptides and/or cells.

Suitable diluents for nucleic acids include but are not limited to water, saline solutions and ethanol.

In an embodiment, the composition is a pharmaceutical composition comprising any of the antibodies, nucleic acids or vectors disclosed herein, and optionally comprising a pharmaceutically acceptable vehicle such as a diluent or carrier.

The compositions described herein can be prepared by per se known methods for the preparation of pharmaceutically acceptable compositions that can be administered to subjects, such that an effective quantity of the active substance is combined in a mixture with a pharmaceutically acceptable vehicle.

Pharmaceutical compositions include, without limitation, lyophilized powders or aqueous or non-aqueous sterile injectable solutions or suspensions, which may further contain antioxidants, buffers, bacteriostats and solutes that render the compositions substantially compatible with the tissues or the blood of an intended recipient. Other components that may be present in such compositions include water, surfactants (such as Tween), alcohols, polyols, glycerin and vegetable oils, for example. Extemporaneous injection solutions and suspensions may be prepared from sterile powders, granules, tablets, or concentrated solutions or suspensions. The composition may be supplied, for example, but not by way of limitation, as a lyophilized powder which is reconstituted with sterile water or saline prior to administration to the patient.

Pharmaceutical compositions may comprise a pharmaceutically acceptable carrier. Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, ethanol, N-(1(2,3-dioleyloxy)propyl)N,N,N-trimethylammonium chloride (DOTMA), diolesylphosphotidyl-ethanolamine (DOPE), and liposomes. Such compositions should contain a therapeutically effective amount of the compound, together with a suitable amount of carrier so as to provide the form for direct administration to the patient.

The composition may be in the form of a pharmaceutically acceptable salt which includes, without limitation, those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylarnino ethanol, In an embodiment, the composition comprises an antibody described herein. In another embodiment, the composition comprises an antibody described herein and a diluent. In an embodiment, the composition is a sterile composition.

A further aspect includes an antibody complex comprising an antibody described herein bound to an LRP protein, e.g., LRP5 or LRP6. The complex may be in solution or comprised in a tissue, optionally in vitro.

Also provided are methods for making and using the regents described herein.

VII. Kits

Another aspect is a kit or package comprising any of the antibodies, immunoconjugates, nucleic acid molecules, vectors, recombinant cells and/or compositions comprised herein. The antibodies, immunoconjugates, nucleic acid molecules, vectors, recombinant cells and/or compositions can be comprised in a vial such as a sterile vial or other housing. As used herein, the term "kit" refers to a collection of items intended for use together. The kit can optionally include a reference agent and/or instructions for use thereof. A kit can further include a shipping container adapted to hold a container, such as a vial, that contains a composition as disclosed herein.

VIII. Methods of Using Antibodies

Antibodies described herein can be used in a number of in vitro and in vivo methods.

A. Methods of Detecting Expression of LRP6

As demonstrated herein, the antibodies can be used to detect LRP6 expression.

Accordingly, the disclosure provides in one aspect, a method of detecting LRP6 expression, the method comprising contacting a sample comprising one or more cells with one or more antibody or immunoconjugates described herein under conditions permissive for forming an antibody: LRP6 complex and detecting the presence of any antibody complex. Typically, the antibody is part of an immunoconjugate comprising an antibody coupled to a detectable label.

The sample can comprise viable cells or a cell extract. The antibody: LRP6 complex can be detected immunoassays such as immunofluorescence, flow cytometry, Western blots, ELISA, SPR and immunoprecipitation followed by SDS-PAGE immunocytochemistry. In some embodiments, the detection is by immunofluorescence. In some embodiments, the detection is by flow cytometry.

As demonstrated herein, a number of the antibodies identified preferentially recognize LRP6. Accordingly, in embodiments wherein the method is for detecting LRP6 expression, the antibody or immunoconjugate comprises a CDR sequence set corresponding to an antibody selected from LRP6-A1, LRP6-A10, LRP6-B6, LRP6-E3, LRP6-G3, LRP6-G9.

B. Methods of Inhibiting WNT Binding to LRP6

Antibodies disclosed herein inhibit binding of Wnt to LRP proteins, in particular, to LRP6. Without wishing to be limited by theory, inhibition of Wnt binding to LRP6 impacts signal transduction induced by the binding of the particular Wnt ligand. For example, antibody binding to LRP6 receptors inhibits LRP6 promotion of beta-catenin phosphorylation. Because phosphorylated beta-catenin is marked for destruction in a cell, the non-phosphorylated form builds up. Accumulation of beta-catenin is associated with malignancy.

It can be desirable to reduce or inhibit Wnt ligand signaling through LRP6. Accordingly, another aspect is a method of inhibiting Wnt ligand binding to a LRP6 or Wnt induced transcriptional activity comprising contacting one or more cells expressing one or more LRP6 polypeptides with an effective amount of an antibody or immunoconjugate described herein.

In an embodiment, the antibody or immunoconjugate comprises a CDR sequence set (full, light chain or heavy chain) corresponding to an antibody selected from LRP6-A1, LRP6-A10, LRP6-B6, LRP6-E3, LRP6-G3, LRP6-G9.

The contacting can for example, be done in vivo by administering an antibody or immunoconjugate to the subject. Such inhibition may be desirable particularly where Wnt signaling is dysregulated as in cancer cells.

C. Methods of Potentiating WNT Signaling Pathways

Certain antibodies that block binding of Wnt ligands to the Wnt3a binding site of LRP5 or LRP6 potentiate the signaling activity of Wnt ligands binding to the non-Wnt3a binding site. Similarly, certain antibodies that block binding of Wnt ligands to the non-Wnt3a binding site of LRP5 or LRP6 potentiate the signaling activity of Wnt ligands binding to the Wnt3a binding site. The blocking activity may be competitive or allosteric. Accordingly, provided herein are methods of potentiating the signaling activity of Wnt-ligand binding to a Wnt3a binding site of LRP5 or LRP6 by contacting LRP5 or LRP6 with an antibody that blocks binding of Wnt ligands to the non-Wnt3a binding site of LRP5 or LRP6. Also provided herein are provided herein are methods of potentiating the signaling activity of Wnt-ligand binding to a non-Wnt3a binding site of LRP5 or LRP6 by contacting LRP5 or LRP6 with an antibody that block binding of Wnt ligands to the Wnt3a binding site of LRP5 or LRP6. Contacting can be performed in vitro or in vivo. In vivo contacting can comprise administering to the subject the appropriate anti-LRP5 or anti-LRP6 antibody.

For example, antibodies comprising CDR sequence sets from antibodies LRP6-A10 or LRP6-B6 are useful for potentiating signaling activity of Wnt-ligand binding to non-Wnt3a binding site of LRP5 or LRP6. Antibodies comprising CDR sequence sets from antibodies LRP6-G3 and LRP6-G9, and possibly LRP6-A1 and LRP6-E3 are useful for potentiating signaling activity of Wnt-ligand binding to Wnt3a binding site of LRP5 or LRP6.

D. Methods and Uses for Treating Cancer

Methods of treating cancer comprise use of or administering to a subject in need thereof a pharmaceutical composition comprising an antibody of this disclosure that binds to LRP6. The subject in thereof can be a subject, e.g., a person, suffering from cancer, or at risk of cancer, such as recurrence of cancer.

In one embodiment, the cancer is selected from acute myeloid leukemia, prostate cancer, glioblastoma, bladder cancer and cervical cancer.

In another embodiment, the cancer cells are selected from brain cancer, breast cancer, colon cancer, endometrial cancer, esophageal cancer, kidney cancer, liver cancer, lung cancer, ovarian cancer, skin cancer, stomach cancer and testicular cancer.

Without wishing to be limited by theory, such therapy may function by inhibiting activation of the canonical Wnt pathway, for example, by inhibiting Wnt binding to LRP6, by inhibiting Wnt-induced transcriptional activity, by inhibiting activation of disheveled, by inhibiting inhibition of the beta-catenin destruction complex and by promoting accumulation of beta-catenin.

As LRP5 and/or LRP6 are often upregulated in cancer, the disclosure in another aspect includes a method for treating cancer, the method comprising administering an effective amount of an antibody or immunoconjugate that specifically binds LRP5 or LRP6 in at least one assay, and inhibits Wnt3a-induced signalling in at least one assay to a subject in need thereof. The disclosure also includes use of an effective amount of an antibody or immunoconjugate that specifically binds LRP5 or LRP6 in at least one assay, and inhibits Wnt3a-induced signalling in at least one assay for treating cancer or in the manufacture of a medicament for treating cancer. The disclosure further includes an effective amount of an antibody or immunoconjugate that specifically binds LRP5 or LRP6 in at least one assay, and inhibits Wnt3a-induced signalling in at least one assay for use in treating cancer.

In an embodiment, antibody or immunoconjugate, e.g., an antibody-drug conjugate, is comprised in a pharmaceutical composition.

In an embodiment, the cancer is selected from brain cancer, breast cancer, colon cancer, endometrial cancer, esophageal cancer, kidney cancer, liver cancer, lung cancer, ovarian cancer, skin cancer, stomach cancer and testicular cancer. In an embodiment, the antibody or immunoconjugate comprises a CDR sequence set corresponding to an antibody selected from LRP6-A1, LRP6-A10, LRP6-B6, LRP6-E3, LRP6-G3, LRP6-G9.

As demonstrated herein, the antibodies are also able to inhibit cancer cell proliferation, Accordingly, also provided is a method for inhibiting cancer cell proliferation comprising contacting one or more cancer cells expressing an LRP6 with an effective amount of an antibody or immunoconjugate that specifically binds LRP6 in at least one assay, and inhibits Wnt3a-induced signalling in at least one assay.

In one embodiment, a method of treating cancer comprises administering to antibodies or immunoconjugate comprising antibody, wherein, the first antibody blocks binding of a Wnt ligand to a Wnt3a binding site of LRP5 or LRP6, and a second antibody blocks binding of a Wnt ligand to a non-Wnt3a binding site of the LRP5 or LRP6 to a subject in need thereof. The disclosure also provided antibodies or immunoconjugate comprising antibody, wherein a first antibody blocks binding of a Wnt ligand to a Wnt3a binding site of LRP5 or LRP6, and a second antibody blocks binding of a Wnt ligand to a non-Wnt3a binding site of the LRP5 or LRP6 for use in treating cancer. The disclosure further provides a use of antibodies or immunoconjugate comprising antibody, wherein a first antibody blocks binding of a Wnt ligand to a Wnt3a binding site of LRP5 or LRP6, and a second antibody blocks binding of a Wnt ligand to a non-Wnt3a binding site of the LRP5 or LRP6 for treating cancer. The disclosure yet also provides a use of antibodies or immunoconjugate comprising antibody, wherein a first antibody blocks binding of a Wnt ligand to a Wnt3a binding site of LRP5 or LRP6, and a second antibody blocks binding of a Wnt ligand to a non-Wnt3a binding site of the LRP5 or LRP6 in the manufacture of a medicament for treating cancer.

In an embodiment, the antibody or immunoconjugate is the antibody or immunoconjugate described herein, for example, an antibody or immunoconjugate that comprises a CDR sequence set (full, light chain or heavy chain) corresponding to an antibody selected from LRP6-A1, LRP6-A10, LRP6-B6, LRP6-E3, LRP6-G3, LRP6-G9.

IX. Methods of Administration

The anti-LRP antibodies of the invention can efficiently deliver a therapeutic composition to cells undergoing Wnt signaling in vivo. In some embodiments, the method of treatment comprises administering to an individual an effective amount of a therapeutic anti-LRP conjugate, e.g., an anti-LRP antibody attached to a therapeutic agent. In some embodiments, the individual has been diagnosed with cancer. In some embodiments, the individual is receiving or has received cancer therapy, e.g., surgery, radiotherapy, or chemotherapy. In some embodiments, the individual has been diagnosed, but the cancer is in remission.

In some embodiments, the anti-LRP conjugate includes a liposome. In some embodiments, the method further comprises monitoring the individual for progression of the cancer. In some embodiments, the dose of the anti-LRP conjugate for each administration is determined based on the therapeutic progress of the individual, e.g., where a higher dose of chemotherapeutic is administered if the individual is not responding sufficiently to therapy.

In some embodiments, the invention can include an antibody or antibody-targeted composition and a physiologically (i.e., pharmaceutically) acceptable carrier. The term "carrier" refers to a typically inert substance used as a diluent or vehicle for a diagnostic or therapeutic agent. The term also encompasses a typically inert substance that imparts cohesive qualities to the composition. Physiologically acceptable carriers can be liquid, e.g., physiological saline, phosphate buffer, normal buffered saline (135-150 mM NaCl), water, buffered water, 0.4% saline, 0.3% glycine, glycoproteins to provide enhanced stability (e.g., albumin, lipoprotein, globulin, etc.), and the like. Since physiologically acceptable carriers are determined in part by the particular composition being administered as well as by the particular method used to administer the composition, there are a wide variety of suitable formulations of pharmaceutical compositions of the present invention (See, e.g., Remington's Pharmaceutical Sciences, 17th ed., 1989).

The compositions of the present invention may be sterilized by conventional, well-known sterilization techniques or may be produced under sterile conditions. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents, wetting agents, and the like, e.g., sodium acetate, sodium lactate, sodium chloride, potassium chloride, calcium chloride, sorbitan monolaurate, and triethanolamine oleate. Sugars can also be included for stabilizing the compositions, such as a stabilizer for lyophilized antibody compositions.

Dosage forms can be prepared for mucosal (e.g., nasal, sublingual, vaginal, buccal, or rectal), parenteral (e.g., subcutaneous, intravenous, intramuscular, or intraarterial injection, either bolus or infusion), oral, or transdermal administration to a patient. Examples of dosage forms include, but are not limited to: dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

Injectable (e.g., intravenous) compositions can comprise a solution of the antibody or antibody-targeted composition suspended in an acceptable carrier, such as an aqueous carrier. Any of a variety of aqueous carriers can be used, e.g., water, buffered water, 0.4% saline, 0.9% isotonic saline, 0.3% glycine, 5% dextrose, and the like, and may include glycoproteins for enhanced stability, such as albumin, lipoprotein, globulin, etc. Often, normal buffered saline (135-150 mM NaCl) will be used. The compositions can contain pharmaceutically acceptable auxiliary substances to approximate physiological conditions, such as pH adjusting and buffering agents, tonicity adjusting agents, wetting agents, e.g., sodium acetate, sodium lactate, sodium chloride, potassium chloride, calcium chloride, sorbitan monolaurate, triethanolamine oleate, etc. In some embodiments, the antibody-targeted composition can be formulated in a kit for intravenous administration.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Injection solutions and suspensions can also be prepared from sterile powders, granules, and tablets. In the practice of the present invention, compositions can be administered, for example, by intravenous infusion, topically, intraperitoneally, intravesically, or intrathecally. Parenteral administration and intravenous administration are the preferred methods of administration. The formulations of targeted compositions can be presented in unit-dose or multi-dose sealed containers, such as ampoules and vials.

The targeted delivery composition of choice, alone or in combination with other suitable components, can be made into aerosol formulations ("nebulized") to be administered via inhalation. Aerosol formulations can be placed into pressurized acceptable propellants, such as dichlorodifluoromethane, propane, and nitrogen.

The pharmaceutical preparation can be packaged or prepared in unit dosage form. In such form, the preparation is subdivided into unit doses containing appropriate quantities of the active component, e.g., according to the dose of the therapeutic agent or concentration of antibody. The unit dosage form can be a packaged preparation, the package containing discrete quantities of preparation. The composition can, if desired, also contain other compatible therapeutic agents.

The antibody (or antibody-targeted composition) can be administered by injection or infusion through any suitable route including but not limited to intravenous, subcutaneous, intramuscular or intraperitoneal routes. An example of administration of a pharmaceutical composition includes storing the antibody at 10 mg/ml in sterile isotonic aqueous saline solution for injection at 4° C., and diluting it in either 100 ml or 200 ml 0.9% sodium chloride for injection prior to administration to the patient. The antibody is administered by intravenous infusion over the course of 1 hour at a dose of between 0.2 and 10 mg/kg. In other embodiments, the antibody is administered by intravenous infusion over a period of between 15 minutes and 2 hours. In still other embodiments, the administration procedure is via subcutaneous bolus injection.

The dose of antibody is chosen in order to provide effective therapy for the patient and is in the range of less than 0.1 mg/kg body weight to about 25 mg/kg body weight or in the range 1 mg-2 g per patient. In some cases, the dose is in the range 1-100 mg/kg, or approximately 50 mg-8000 mg/patient. The dose may be repeated at an appropriate frequency which may be in the range once per day to once every three months, depending on the pharmacokinetics of the antibody (e.g., half-life of the antibody in the circulation) and the pharmacodynamic response (e.g., the duration of the therapeutic effect of the antibody). In some embodiments, the in vivo half-life of between about 7 and about 25 days and antibody dosing is repeated between once per week and once every 3 months.

Administration can be periodic. Depending on the route of administration, the dose can be administered, e.g., once every 1, 3, 5, 7, 10, 14, 21, or 28 days or longer (e.g., once every 2, 3, 4, or 6 months). In some cases, administration is more frequent, e.g., 2 or 3 times per day. The patient can be monitored to adjust the dosage and frequency of administration depending on therapeutic progress and any adverse side effects, as will be recognized by one of skill in the art.

Thus, in some embodiments, additional administration is dependent on patient progress, e.g., the patient is monitored between administrations. For example, after the first administration or round of administrations, the patient can be monitored for rate of tumor growth, recurrence (e.g., in the case of a post-surgical patient), or general disease-related symptoms such as weakness, pain, nausea, etc.

In therapeutic use for the treatment of cancer, an antibody-targeted composition (e.g., including a therapeutic and/or diagnostic agent) can be administered at the initial dosage of about 0.001 mg/kg to about 1000 mg/kg daily and adjusted over time. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosage is varied depending upon the requirements of the patient, the severity of the condition being treated, and the targeted composition being employed. For example, dosages can be empirically determined considering the type and stage of cancer diagnosed in a particular patient. The dose administered to a patient, in the context of the present invention, should be sufficient to affect a beneficial therapeutic response in the patient over time. The size of the dose will also be determined by the existence, nature, and extent of any adverse side-effects that accompany the administration of a particular targeted composition in a particular patient, as will be recognized by the skilled practitioner.

The above disclosure generally describes the present disclosure. A more complete understanding can be obtained by reference to the following specific examples. These examples are described solely for the purpose of illustration and are not intended to limit the scope of the application. Changes in form and substitution of equivalents are contemplated as circumstances might suggest or render expedient. Although specific terms have been employed herein, such terms are intended in a descriptive sense and not for purposes of limitation.

EXEMPLARY EMBODIMENTS

1. An antibody that specifically binds LRP6, comprising a light chain variable region and/or a heavy chain variable region, the heavy chain variable region comprising complementarity determining regions CDR-H1, CDR-H2 and CDR-H3, the light chain variable region comprising complementarity determining region CDR-L1, CDR-L2 and CDR-L3, wherein the amino acid sequences of said CDRs comprise or consist of sequences selected from: CDR sequence sets of anti-LRP6 antibodies: LRP6-A1, LRP6-A10, LRP6-B6, LRP6-E3, LRP6-G3, and LRP6-G9.

2. The antibody of embodiment 1 wherein the amino acid sequences of said CDRs comprise or consist of sequences selected from the sequences as set forth below:

CDR-H1 is selected from the group consisting of LSYYYI (SEQ ID NO: 2); ISYSSI (SEQ ID NO: 25); LYYYSM (SEQ ID NO: 4); ISSYYI (SEQ ID NO: 5) and IYSYYI (SEQ ID NO: 26);

CDR-H2 is selected from the group consisting of SIYSSYGYTS (SEQ ID NO: 6); YISSYYGYTY (SEQ ID NO: 7); SISPYYGYTY (SEQ ID NO: 8); SIYSSYGYTY (SEQ ID NO: 9) and SIYSSYSYTS (SEQ ID NO: 27);

CDR-H3 is selected from the group consisting of TVRGSKKPYFSGWAM (SEQ ID NO: 10); AHYFPWAGAM (SEQ ID NO: 11);

43

SSYFPWFSAM (SEQ ID NO: 12); YAGYYYYP-WAYYGWPFSGL (SEQ ID NO: 13).

CDR-L1 is SVSSA (SEQ ID NO: 14);

CDR-L2 is SASSLYS (SEQ ID NO: 15); and/or

CDR-L3 is selected from the group consisting of YYSPI (SEQ ID NO: 16), YSWGPF (SEQ ID NO: 17), YYFLI (SEQ ID NO: 18), AGSAPYHLI (SEQ ID NO: 19), and YYWPI (SEQ ID NO: 20).

3. The antibody of embodiment 2, wherein the antibody comprises a heavy chain variable region comprising:

i) a heavy chain amino acid sequence as set forth in Table 2;

ii) an amino acid sequence with at least 50%, at least 60%, at least 70%, at least 80%, at least 90%, at least 95%, at least 98% or at least 99% sequence identity to the heavy chain amino acid sequence as set forth in Table 2, wherein the CDR sequences are a CDR sequence set as set forth in Table 1, or iii) a conservatively substituted amino acid sequence of i) wherein the CDR sequences are a CDR sequence set as set forth in Table 1.

4. The antibody of any one of embodiments 2 to 4, wherein the antibody comprises a light chain variable region comprising:

i) a light chain amino acid sequence as set forth in Table 2, ii) an amino acid sequence with at least 50%, at least 60%, at least 70%, at least 80%, at least 90%, at least 95%, at least 98% or at least 99% sequence identity to the light chain amino acid sequence as set forth in Table 2, wherein the CDR sequences are a CDR sequence set as set forth in Table 1, or iii) a conservatively substituted amino acid sequence of i) wherein the CDR sequences are a CDR sequence set as set forth in Table 1.

5. The antibody of any one of embodiments 1-4, wherein the CDR sequences are a full CDR sequence set selected from an antibody identified in Table 1.

6. The antibody of any one of embodiments 1 to 5, wherein the antibody cross-reacts with LRP5.

7. The antibody of embodiment 1, wherein the CDR sequences comprise a light chain CDR sequence set or a heavy chain CDR sequence set selected from an antibody identified in Table 1.

8. The antibody of any of embodiments 1 to 7, wherein the antibody specifically binds LRP6.

9. The antibody of embodiment 8, wherein the CDR sequences are a CDR sequence set of an antibody selected from antibodies LRP6-A1, LRP6-A10, LRP6-B6, LRP6-E3, LRP6-G3, and LRP6-G9.

10. The antibody of embodiments 1 to 9, which blocks binding of a Wnt ligand to the Wnt3a binding site of LRP6.

11. The antibody of embodiments 1 to 9, which blocks binding of a Wnt ligand to the non-Wnt3a binding site of LRP6.

12. The antibody of any one of embodiments 1 to 11, wherein the antibody is a monoclonal antibody.

13. The antibody of any one of embodiments 1 to 12, wherein the antibody is a humanized antibody.

14. The antibody of any one of embodiments 1 to 13, wherein the antibody is a single chain antibody.

15. The antibody of any one of embodiments 1 to 14, wherein the antibody is an antibody binding fragment selected from Fab, Fab', F(ab')2, scFv, dsFv, ds-scFv, dimers, nanobodies, minibodies, diabodies, and multimers thereof.

16. The antibody of any one of embodiments 1 to 14, wherein the antibody is a bi-specific antibody.

17. The antibody of any one of embodiments 1 to 14, wherein the antibody is a bi-specific antibody that further binds to FZD receptor.

18. The antibody of any one of embodiments 1 to 17, comprising a non-natural glycosylation pattern.

19. The antibody of any one of embodiments 1 to 17, comprising a cysteine substitution or addition, e.g., in the constant region or a framework region.

20. An immunoconjugate comprising the antibody of any one of embodiments 1 to 17, and a detectable label or cytotoxic agent.

21. The immunoconjugate of embodiment 20, comprising a cytotoxic agent selected from maytansinoid, auristatin, dolastatin, tubulysin, cryptophycin, pyrrolobenzodiazepine (PBD) dimer, indolinobenzodiazepine dimer, alpha-amanitin, trichothene, SN-38, duocarmycin, CC1065, calicheamincin, an enediyne antibioatic, taxane, doxorubicin derivatives, anthracycline and stereoisomers, azanofide, isosteres, analogs or derivatives thereof.

22. A nucleic acid molecule encoding the antibody of any one of embodiments 1 to 17.

23. The nucleic acid molecule of embodiment 22, wherein one or more of the CDR sequences is/are encoded by a nucleic acid in Table 2.

24. The nucleic acid molecule of embodiment 22, wherein the antibody comprises a heavy chain variable region encoded by a nucleic acid comprising:

i) a heavy chain nucleic acid sequence as set forth in Table 2;

ii) a nucleotide sequence with at least 50%, at least 60%, at least 70%, at least 80%, at least 90%, at least 95%, at least 98% or at least 99% sequence identity to the heavy chain nucleic acid sequence as set forth in Table 2, wherein the CDR sequences are a CDR sequence set as set forth in Table 1, or iii) a codon degenerate nucleic acid sequence of i) wherein the CDR sequences are a CDR sequence set as set forth in Table 1.

25. The nucleic acid molecule of embodiment 22, wherein the antibody comprises a light chain variable region encoded by a nucleic acid comprising:

i) a light chain nucleic acid sequence as set forth in Table 2, ii) a nucleic acid sequence with at least 50%, at least 60%, at least 70%, at least 80%, at least 90%, at least 95%, at least 98% or at least 99% sequence identity to the light chain nucleic acid sequence as set forth in Table 2, wherein the CDR sequences are a CDR sequence set as set forth in n Table 1, or iii) a codon degenerate nucleic acid sequence of i) wherein the CDR sequences are a CDR sequence set as set forth in Table 1.

26. A vector comprising an expression control sequence operatively linked to the nucleic acid of any one of embodiments 22 to 25.

27. A host cell comprising recombinant nucleic acid molecule comprising an expression control sequence operatively linked to the nucleic acid of any of embodiments 22-26.

28. The host cell of embodiment 27, that is a Chinese Hamster Ovary (CHO) cell.

29. A host cell comprising the vector of embodiment 26.

30. A method for making an anti-LRP6 antibody comprising culturing a host cell of any one of embodiments 27 to 29.

31. A composition comprising the antibody of any one or more of embodiments 1 to 17, immunoconjugate of embodiments 20-21, the nucleic acid molecule of embodiments 22-25, the vector of embodiment 26, or host cell of embodiment 29, optionally with a suitable diluent.

32. The composition of embodiment 31, wherein the composition comprises one or more antibodies or immunoconjugates, optionally wherein the composition is a pharmaceutical composition.

33. A kit comprising the antibody of any one or more of embodiments 1 to 17, immunoconjugate of embodiments 20-21, the nucleic acid molecule of embodiments 22-25, the vector of embodiment 26, or host cell of embodiments 29-29.

34. A method of detecting LRP6 expression, the method comprising contacting a sample comprising one or more cells with one or more antibody or immunoconjugate of any one of embodiments 1 to 21 under conditions permissive for forming an antibody:cell complex and detecting the presence of any antibody complex.

35. The method of embodiment 34, wherein the detection is by immunofluorescence.

36. The method of embodiment 34, wherein the detection is by flow cytometry.

37. The method of any one of embodiments 34 to 36, wherein the method is for detecting LRP4 expression and the antibody or immunoconjugate comprises a CDR sequence set corresponding to an antibody selected from LRP6-A1, LRP6-A10, LRP6-B6, LRP6-E3, LRP6-G3, and LRP6-G9.

38. A method of inhibiting Wnt ligand binding to an LRP6 receptor, disrupting a Wnt signaling pathway, inhibiting Wnt-induced transcriptional activity, inhibiting activation of disheveled, promoting preservation of the beta-catenin destruction complex, promoting accumulation of beta-catenin or inhibiting growth of a cell, the method comprising contacting a cell expressing a LRP6 receptor with an antibody or immunoconjugate of any one of embodiments 1 to 21.

39. The method of embodiment 38, wherein the antibody or immunoconjugate blocks binding of a Wnt ligand to a Wnt3a binding site of LRP6.

40. The method of embodiment 38, wherein the antibody or immunoconjugate blocks binding of a Wnt ligand to a non-Wnt3a binding site of LRP6.

41. The method of embodiment 38, wherein the antibody or immunoconjugate comprises a CDR sequence set corresponding to an antibody selected from the group consisting of LRP6-A1, LRP6-A10, LRP6-B6, LRP6-E3, LRP6-G3, and LRP6-G9.

42. A method of treating cancer in a subject in need thereof comprising administering to the subject an effective amount of a pharmaceutical composition comprising an antibody or an immunoconjugate of any one or more of embodiments 1 to 21.

43. The method of embodiment 42, wherein the cancer is selected from colon, lung, breast ovarian, endometrial, pancreas, stomach, liver, adrenocortical carcinoma and osteoblastoma cancer cells.

44. The method of embodiment 42, wherein the cancer is selected from acute myeloid leukemia, prostate cancer, glioblastoma, bladder cancer and cervical cancer.

45. The method of embodiment 42, comprising administering to the subject first and second antibodies or antibody conjugates of any one of embodiments 1 to 21, wherein the first blocks binding of a Wnt ligand to a Wnt3a binding site of LRP6, and the second blocks binding of a Wnt ligand to a non-Wnt3a binding site of LRP6.

46. The method of embodiment 45, wherein the first antibody or immunoconjugate comprises a CDR sequence set selected from antibodies LRP6-A10 or LRP6-B6 and the second antibody or immunoconjugate comprises a CDR sequence set selected from antibodies LRP6-A1, LRP6-A10, LRP6-B6, LRP6-E3, LRP6-G3, or LRP6-G9.

47. The method of embodiment 42, wherein the antibody or immunoconjugate that specifically binds LRP6 in at least one assay, and inhibits Wnt3a-induced signaling in at least one assay, optionally wherein the antibody or immunoconjugate is the antibody or immunoconjugate of any one of embodiments 1 to 21.

48. The method of embodiment 42, wherein the antibody or immunoconjugate comprises a CDR sequence set corresponding to an antibody selected from the group consisting of LRP6-A1, LRP6-A10, LRP6-B6, LRP6-E3, LRP6-G3, and LRP6-G9.

49. A method of potentiating the signaling activity of Wnt-ligand binding to a Wnt3a binding site of LRP6 comprising contacting a cell expressing LRP6 with an antibody that blocks binding of Wnt ligands to the non-Wnt3a binding site of LRP6.

50. A method of potentiating the signaling activity of Wnt-ligand binding to a non-Wnt3a binding site of LRP6 by contacting a cell expressing LRP6 with an antibody that blocks binding of Wnt ligands to the Wnt3a binding site of LRP6.

51. The method of any of embodiment 49 or 50, performed in vitro.

52. The method of any of embodiment 49 or 50, performed in vivo.

The following non-limiting examples are illustrative of the present disclosure:

EXAMPLES

Example 1

Phage Display Antibody Library

Phage-displayed antibody libraries are a powerful technology for the generation of therapeutic antibodies[17,18]. Highly complex libraries of $>10^{10}$ independent antibody fragments are displayed on phage particles as coat protein fusion molecules and screened to isolate antibodies that recognize antigens of interest. The inventors have established synthetic antibody libraries with antigen-binding sites constructed entirely from engineered sequences. The resulting antibodies use an optimized human framework, and are thus minimally immunogenic when used as potential therapeutics. The synthetic antibodies are highly stable, and their human framework and antigen combining sites can be tailored to optimize affinity, specificity and efficacy.

Characterization and Optimization of Anti-LRP6 Antibodies

Example 2

Novel synthetic anti-LRP6 antibodies were identified from the Fab-phage library described in Example 1 using immobilized recombinant LRP6-ECD (extracellular domain). Fab-phage clones from round 4 were screened for binding by ELISA and the amino acid sequences of the CDRs of the positive binders are present in FIG. 1A. The complete DNA and amino acid sequences of the variable region (heavy and light chains) of the binders are presented in the specification, above. Epitope mapping by competitive ELISA reveals that the antibodies bind to two unique epitopes on the ECD of LRP6. LRP6-A1, LRP6-G3 and LRP6-G9 bind to a similar epitope while LRP6-A10 and LRP6-B6 share a similar epitope.

The full length IgG1s were purified and a single-point ELISA was done to determine the specificity of the antibodies. As shown in FIG. 1B, 5 out of 6 LRP6 antibodies bind to the recombinant human LRP6-Fc chimera. Interestingly, LRP6-A10 and LRP6-B6 antibodies bind equally well to the recombinant mouse LRP6His chimera while LRP6-A1, LRP6-G3 and LRP6-G9 show partial binding. Furthermore, none of the LRP6 antibodies bound to the recombinant mouse LRP5-His chimera, demonstrating the specificity to LRP6. LRP6-E3 antibody failed to bind to any of the recombinant proteins and was only used as a negative control. A multipoint competitive ELISA was used to determine the relative affinities of the antibodies to the recombinant antigen. The IC50 was determined by non-linear regression analysis and is summarized in Table 3, below. The complete dose response curves and the non-linear regression plots are presented in FIG. 8.

Table 3 reports the IC50 of LRP6 antibodies as determined by competitive ELISA. The log of the recombinant human LRP6-Fc chimera concentration (x-axis) was plotted against the OD450 reading of the antibody (y-axis). The IC50 was determined by non-linear regression analysis.

TABLE 3

| IgG1 antibody | $IC_{50}$ (nM) |
|---|---|
| LRP6-A1 | 9.58 |
| LRP6-A10 | 6.29 |
| LRP6-B6 | 15.28 |
| LRP6-G3 | 10.23 |
| LRP6-G9 | 6.03 |

Figure 9:
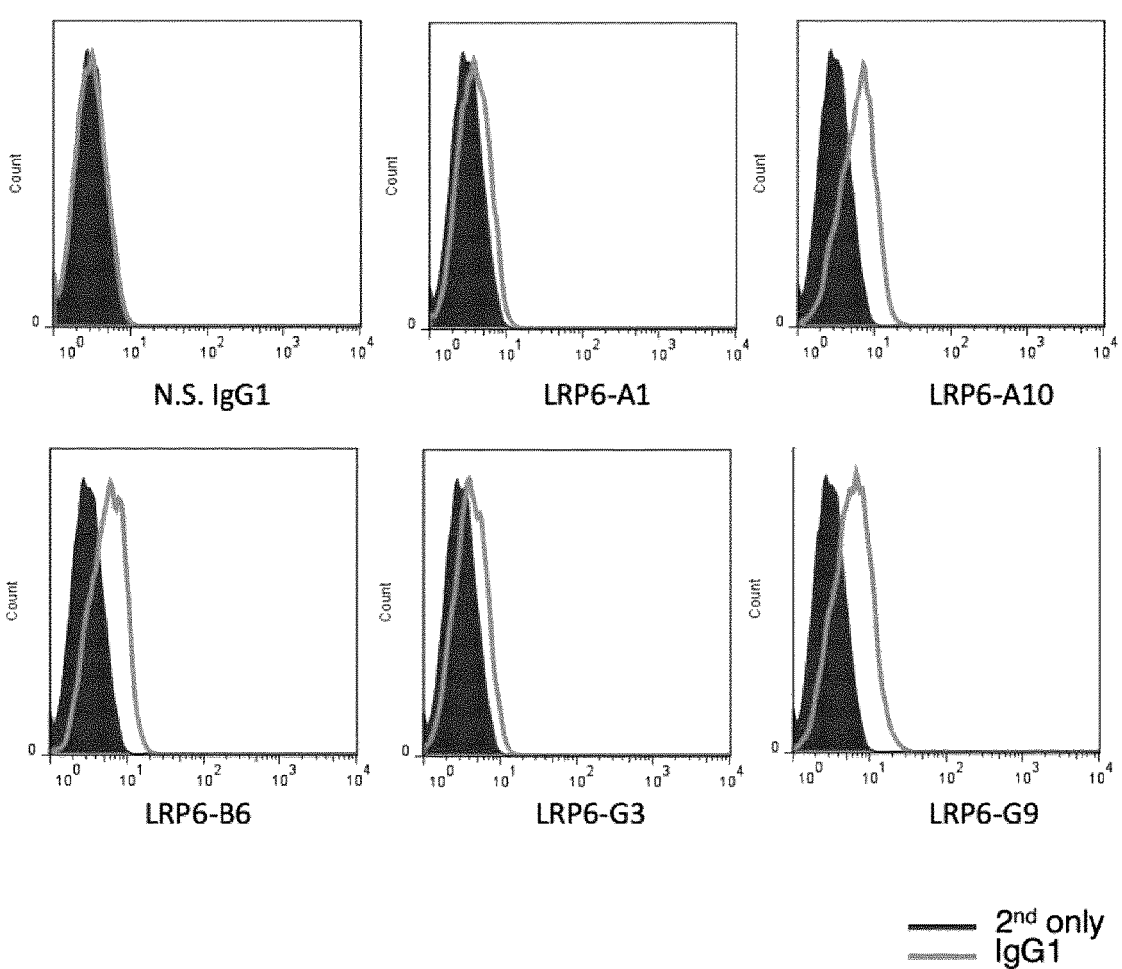
Figure 10:
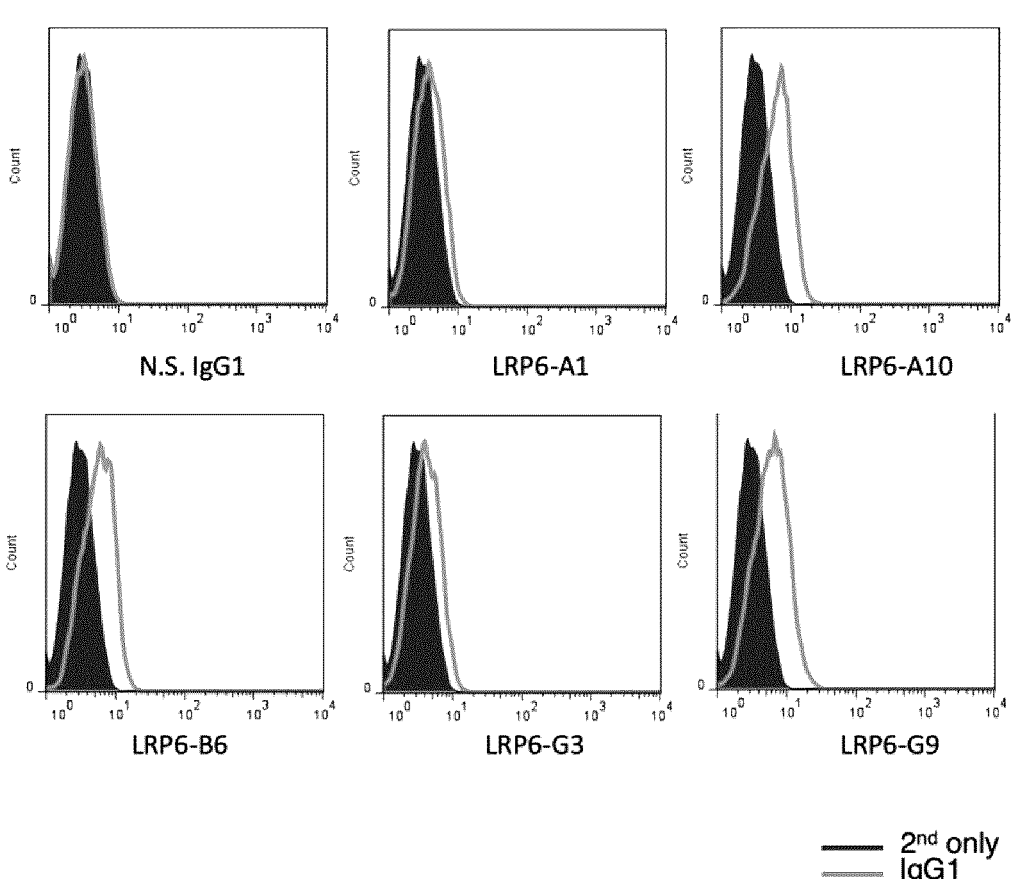
FIG. 10 shows an analysis of IgG1 binding to cell-surface LRP6 by flow cytometry. LRP6 IgG's were tested for binding to breast cancer cell line, T47D. Binding of the anti-LRP6 IgG1 proteins was detected using an Alexa 488-conjugated secondary antibody against F(ab')2. The stained anti-LRP6 population is shown in green and the secondary only stained population is shown in filled blue.

Western blot analysis of whole cell lysates has shown that LRP6 is highly expressed in the NSCLC cell line, H23, and the triple negative breast cancer cell line, MDAMB231. (Triple negative breast cancer cells test negative for estrogen receptors, progesterone receptors and excess Her2 protein.) LRP6 has also been shown to be expressed at low levels in the breast cancer cell line, T47D (data not shown). The LRP6 IgG1 antibodies label the surfaces of H23 (FIG. 2), MDAMB231 (FIG. 9) and T47D (FIG. 9) cells as assessed by FACS analysis and demonstrate that the LRP6 antibodies can bind to the full-length receptor expressed on the surface of these cell lines. As mentioned above, Wnt signaling initiates the canonical pathway, which primarily regulates beta-catenin stability and function.

Upon Wnt stimulation, beta-catenin levels in the cytosol and nucleus rise resulting in an increase in TCF/LEF (transcription factors) mediated transcription. The TOPflash reporter assay is a widely used tool to assess beta-catenin activity in vitro. The vector consists of several TCF/LEF binding sites that drive the expression of the firefly luciferase reporter gene. Several cancer cell lines expressing this reporter were generated in order to assess the functional activity of the LRP6 antibodies in regulating the Wnt-canonical pathway.

As shown in FIG. 3A, conditioned media expressing Wnt3a (Wnt3aCM) induces a 120-fold increase in luciferase reporter activity compared to treatment with control conditioned media (ConCM) in MDAMB231 cells pre-treated with the negative control IgG1, anti-MBP. LRP6-A10 and LRP6-B6 antibodies significantly inhibited the Wnt3aCM-induced reporter activity. In contrast, LRP6-G3 and LRP6-G9 antibodies significantly potentiated the Wnt3aCM-induced reporter activity. A similar result was observed in the breast cancer cell line, T47D (FIG. 3B) and the osteosarcoma cell line, U20S (FIG. 3C). In the U20S cell line, the ConCM- and Wnt3aCM-induced reporter activity was inhibited by LRP6-A10 and LRP6-B6 antibodies while LRP6-G3 and LRP6-G9 antibodies potentiated the reporter activity (compared to anti-MBP (maltose binding protein)). This observation suggests that the U20S cells express endogenous Wnt3a, which may regulate the TCF/LEF-mediated transcriptional activity in the basal state.

Structural and mutagenesis studies have revealed that Wnt3a binds to a domain that is unique from the binding site of the remaining Wnt ligands. Our results suggest that LRP6-A10 and LRP6-B6 antibodies may be binding to the Wnt3a binding site thus blocking TCF/LEF mediated transcription in response to Wnt3aCM. In contrast, LRP6-G3 and LRP6-G9 (and perhaps LRP6-A1) antibodies may bind to the alternative non-Wnt3a binding site. To address this hypothesis, we assessed reporter activity in the NSCLC cell line, H23. Previous studies have shown that Wnt2 primarily drives the basal TCF/LEF mediated transcriptional activity and these cells do not express Wnt3a[19]. As expected, LRP6-A10 and LRP6-B6 antibodies inhibit the Wnt3aCM induced reporter while LRP6-A1, LRP6-G3 and LRP6-G9 antibodies potentiate the Wnt3aCM induced reporter, activity (compared to MBP; FIG. 4A). Interestingly, LRP6-A10 and LRP6-B6 antibodies potentiate the basal (ConCM-induced) reporter activity while LRP6-A1, LRP6-G3 and LRP6-G9 antibodies inhibit the basal (ConCM-induced) reporter activity (compared to MBP). This observation correlates with our earlier hypothesis that the LRP6-A10 and LRP6-B6 antibodies may bind to the Wnt3a binding site while the LRP6-A1, LRP6-G3 and LRP6-G9 antibodies may bind to the alternative non-Wnt3a binding site. To further support this observation, we used the HEK293 cell line that stably expresses the luciferase reporter gene as well as a tetracycline-driven Wnt1 gene. As shown in FIG. 4B, LRP6-A10 antibody significantly inhibits the reporter activity upon stimulation with recombinant Wnt3a while having no effect upon Wnt1 stimulation. LRP6-G3 antibody, in contrast, significantly inhibits the reporter activity upon stimulation with Wnt1 while having no effect upon stimulation with recombinant Wnt3a.

Our observations so far suggest that LRP6-A10 and LRP6-G3 antibodies have the most potent effects on Wnt3aCM-induced reporter activity. To address whether the effects of the antibodies is associated with Wnt3a and not with any other component present in the conditioned medium, we measured reporter activity in the breast cancer cell lines in response to recombinant Wnt3a stimulation. Consistent with our previous observations, LRP6-A10 antibody significantly inhibits the reporter activity upon stimulation with recombinant Wnt3a while LRP6-G3 potentiates the recombinant Wnt3a-stimulated reporter activity (FIG. 5). The calculated $IC_{50}$ for LRP6-A10 antibody as determined by competitive ELISA was 6.29 nM (Table 3). We therefore examined whether we could calculate a functional $IC_{50}$ for LRP6-A10 antibody using the TOPflash reporter assay. LRP6-A10 antibody inhibits the Wnt3aCM-stimulated reporter activity in a dose dependent manner in MDAM8231, U2OS, and H23 cancer cells (FIG. 6A). Interestingly, LRP6-A10 Fab also inhibits Wnt3aCM-stimulated reporter activity in a dose dependent manner in MDAM8231 cells (FIG. 6B). The functional $IC_{50}$ was determined by non-linear regression analysis and is presented in FIG. 5C. Our results show that the LRP6-A10 antibody (both IgG1 and Fab) displays a functional $IC_{50}$ that is greater than the $IC_{50}$ determined from the competitive ELISA (<0.3 nM).

The effects of LRP6-A10 and LRP6-G3 antibodies on the proximal events of Wnt signaling were assessed by western blot analysis (FIG. 7A). H23 cells treated with LRP6-A10 or LRP6-G3 antibodies significantly inhibited ConCM-induced LRP6 phosphorylation. In contrast, only LRP6-A10 antibody reduced Wnt3aCM-induced LRP6 phosphorylation and total LRP6 protein. A similar effect on LRP6 phosphorylation is observed in membrane fractions isolated from H23 cells treated with LRP6-A10 and LRP6-G3 antibodies prior to stimulation with conditioned media (FIG. 7B). LRP6-G3 antibody significantly reduces the Axin1 protein levels in Wnt3aCM-stimulated cells. Since Axin1 is a component of the destruction complex that regulates the "free" pool of beta-catenin level, its diminished expression upon treatment with LRP6-G3 antibody prior to Wnt3aCM stimulation may explain why this antibody effectively potentiates the Wnt3aCM-induced reporter activity (FIGS. 4 & 5).

To get a better understanding of the effects of the antibodies on beta-catenin levels, cytosolic fractions of H23 cells treated with LRP6-A10 and LRP6-G3 antibodies prior to stimulation with conditioned media were isolated. As shown in FIG. 7B, LRP6-A10 antibody significantly upregulates and downregulates beta-catenin levels in ConCM- and Wnt3aCM-treated cells, respectively. Similarly, LRP6-G3 antibody slightly decreases and increases beta-catenin levels in ConCM- and Wnt3aCM-treated cells, respectively.

Figure 8:
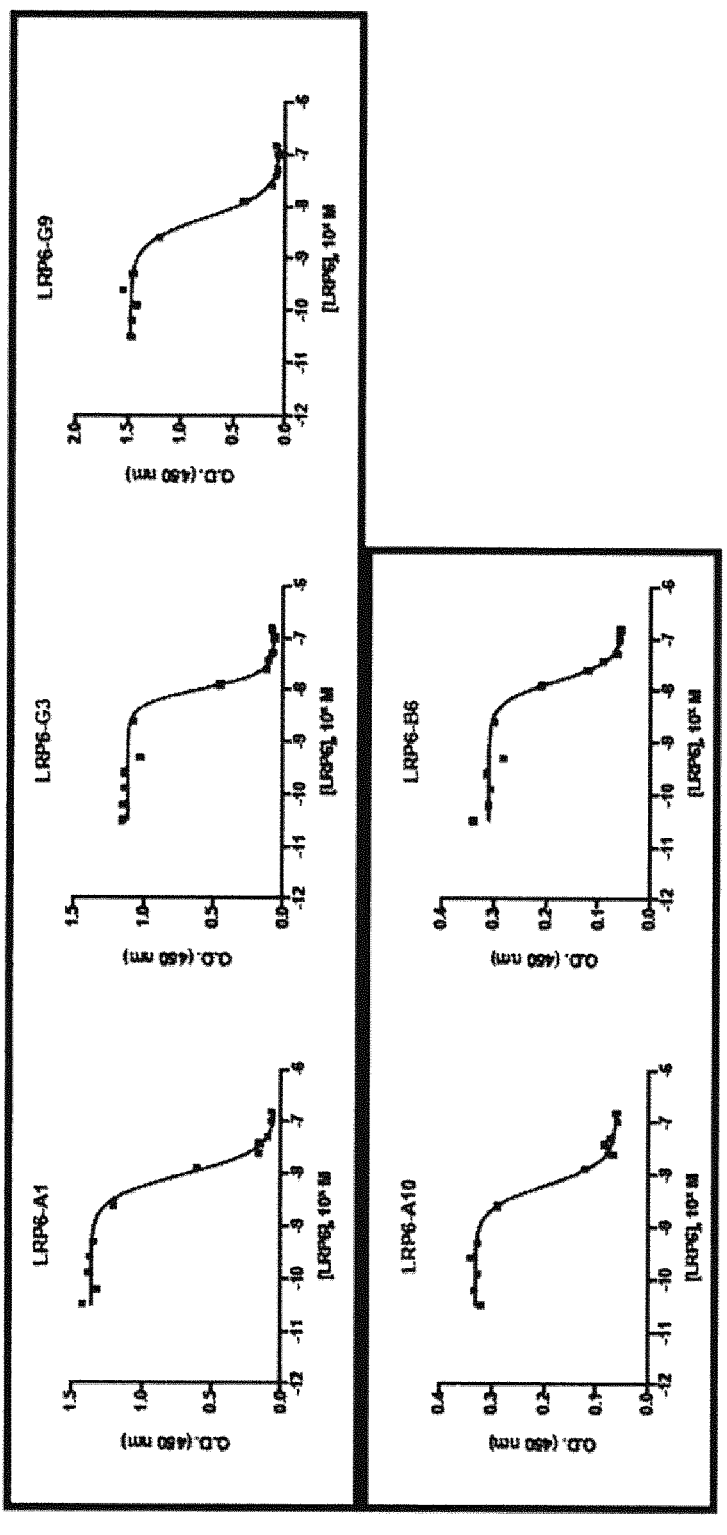
FIG. 8 shows multi-point competitive ELISA. Dose response curves and the non-linear regression plots are for LRP 6 antibodies.

The NSCLC cell line, H23, serves as an excellent system to explore the effects of co-treatment of the LRP6 antibodies on TOPflash reporter activity. Our previous results show that LRP6-A10 antibody potentiates and inhibits the ConCM-induced and Wnt3aCM-induced reporter activity, respectively. In contrast, LRP6-G3 antibody inhibits and potentiates the ConCM-induced and Wnt3aCM-induced reporter activity, respectively. As shown in FIG. 8, LRP6-A10 antibody is unable to potentiate the ConCM-induced reporter activity in the presence of LRP6-G3 antibody. Similarly, LRP6-G3 antibody is unable to potentiate the Wnt3aCM-induced reporter activity in the presence of LRP6-A10 antibody. Observations suggest that the co-treatment of LRP6-A10 and LRP6-G3 antibodies can have a potent inhibitory effect on Wnt-stimulated TCF/LEF-mediated transcription. Thus, by taking advantage of advances in library design strategies, we have been able to discover novel LRP6 antibodies that can exert both antagonistic and potentiating activities on proximal and distal events related to beta-catenin signaling. These activities also depend on the different interactions between Wnt ligands and LRP6. We are actively investigating these antibodies for their therapeutic potential in vitro and in vivo.

| Abbreviations | |
| --- | --- |
| Abbreviation | Complete term |
| APC | Adenomatous polyposis coli |
| CDR | Complementarity determining region |

-continued

| Abbreviations | |
| --- | --- |
| Abbreviation | Complete term |
| CK1 | Casein kinase 1 |
| Dsh/Dvl | Dishevelled |
| ECD | Extracellular domain |
| ELISA | Enzyme-linked immunosorbent assay |
| Fab | Fragment antigen-binding |
| FACS | Fluorescence-activated cell sorting |
| Fc | Fragment crystallizable region |
| GSK3b | Glycogen synthase kinase 3 beta |
| $IC_{50}$ | Half maximal inhibitory concentration |
| IgG1 | Immunoglobulin G 1 |
| LRP | Low-density lipoprotein receptor-related protein |
| OD | Optical density |
| NSCLC | Non-small cell lung carcinoma |

1. Saito-Diaz, K. et al. The way Wnt works: components and mechanism. Growth Factors Chur Switz. 31, 1-31 (2013).

2. Clevers, H. & Nusse, R. Wnt/beta-catenin signaling and disease. Cell 149, 1192-1205 (2012).

3. Anastas, J. N. & Moon, R. T. WNT signaling pathways as therapeutic targets in cancer. Nat. Rev. Cancer 13, 11-26 (2012).

4. Baron, R. & Kneissel, M. WNT signaling in bone homeostasis and disease: from human mutations to treatments. Nat. Med. 19, 179-192 (2013).

5. Kim, W., Kim, M. & Jho, E. Wnt/beta-catenin signaling: from plasma membrane to nucleus, Biochem. J. 450, 9-21 (2013).

6. Chen, S. et al. Structural and Functional Studies of LRP6 Ectodomain Reveal a Platform for Wnt Signaling. Dev. Cell 21, 848-861 (2011).

7. MacDonald, B. T. & He, X. Frizzled and LRP5/6 Receptors for Wnt/beta-Catenin Signaling. Cold Spring Harb. Perspect. Biol. 4, a007880-a007880 (2012).

8. Niehrs, C. & Shen, J. Regulation of LRP6 phosphorylation. Cell. Mel. Life Sci. CMLS 67, 2551-2562 (2010).

9. Williams, B. O. & Insogna, K. L. Where Wnts Went: The Exploding Field of LRP5 and LRP6 Signaling in Bone. J. Bone Miner. Res. 24, 171-178 (2009).

10. Bafico, A, Liu, G., Goldin, L., Harris, V. & Aaronson, S. An autocrine mechanism for constitutive Wnt pathway activation in human cancer cells. Cancer Cell 6, 497-506 (2004).

11. Liu, C.-C., Prior, J., Piwnica-Worms, D. & Bu, G. LRP6 overexpression defines a class of breast cancer subtype and is a target for therapy. Proc. Natl. Acad. Sci. 107, 5136-5141 (2010).

12. Li, Y. & Bu, G. LRP5/6 in Wnt signaling and tumorigenesis. Future Oneel. Lend. Engl. 1, 673-681 (2005).

13. MacDonald, B. T., Semenov, M. V., Huang, H. & He, X. Dissecting Molecular Differences between Wnt Coreceptors LRP5 and LRP6. PLoS ONE 6, e23537 (2011).

14. Mi, K. & Johnson, G. V. W. Role of the intracellular domains of LRP5 and LRP6 in activating the Wnt canonical pathway. J. Cell. Biochem. 95, 328-338 (2005).

15. Ettenberg, S. A et al. Inhibition of tumorigenesis driven by different Wnt proteins requires blockade of distinct ligand-binding regions by LRP6 antibodies. Proc. Natl. Acad. Sci. 107, 15473-15478 (2010).

16. Gong, Y. et al. Wnt Isoform-Specific Interactions with Coreceptor Specify Inhibition or Potentiation of Signaling by LRP6 Antibodies. PLoS ONE 5, e12682 (2010).

17. Lee, C. V. et al. High-affinity human antibodies from phage-displayed synthetic Fab libraries with a single framework scaffold. J. Mel. Biol. 340, 1073-1093 (2004).

18. Sidhu, S. S. & Fellouse, F. A Synthetic therapeutic antibodies. Nat. Chem. Biol. 2, 682-688 (2006).

19. Akiri, G. et al. Wnt pathway aberrations including autocrine Wnt activation occur at high frequency in human non-small-cell lung carcinoma. Oncogene 28, 2163-2172 (2009).

As used herein, the following meanings apply unless otherwise specified. The word "may" is used in a permissive sense (i.e., meaning having the potential to), rather than the mandatory sense (i.e., meaning must). The words "include", "including", and "includes" and the like mean including, but not limited to. The singular forms "a," "an," and "the" include plural referents. Thus, for example, reference to "an element" includes a combination of two or more elements, notwithstanding use of other terms and phrases for one or more elements, such as "one or more." The phrase "at least one" includes "one or more", "one or a plurality" and "a plurality". The term "or" is, unless indicated otherwise, non-exclusive, i.e., encompassing both "and" and "or." The term "any of" between a modifier and a sequence means that the modifier modifies each member of the sequence. So, for example, the phrase "at least any of 1, 2 or 3" means "at least 1, at least 2 or at least 3". The term "consisting essentially of" refers to the inclusion of recited elements and other elements that do not materially affect the basic and novel characteristics of a claimed combination.

It should be understood that the description and the drawings are not intended to limit the invention to the particular form disclosed, but to the contrary, the intention is to cover all modifications, equivalents, and alternatives falling within the spirit and scope of the present invention as defined by the appended claims. Further modifications and alternative embodiments of various aspects of the invention will be apparent to those skilled in the art in view of this description. Accordingly, this description and the drawings are to be construed as illustrative only and are for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed or omitted, and certain features of the invention may be utilized independently, all as would be apparent to one skilled in the art after having the benefit of this description of the invention. Changes may be made in the elements described herein without departing from the spirit and scope of the invention as described in the following claims. Headings used herein are for organizational purposes only and are not meant to be used to limit the scope of the description.

All publications, patents, and patent applications mentioned in this specification are herein incorporated by reference to the same extent as if each individual publication, patent, or patent application was specifically and individually indicated to be incorporated by reference.

---

What is claimed is:

1. An antibody that specifically binds LRP6, comprising a light chain variable region and a heavy chain variable region, the heavy chain variable region comprising complementarity determining regions CDR-H1, CDR-H2 and CDR-H3, the light chain variable region comprising complementarity determining region CDR-L1, CDR-L2 and CDR-L3, wherein the amino acid sequences of said CDR sequences are a full CDR sequence set selected from the following sets of CDR sequences:

a) CDR-H1 of SEQ ID NO:02, CDR-H2 of SEQ ID NO:06, CDR-H3 of SEQ ID NO:10 and CDR-L1 of SEQ ID NO:14, CDR-L2 of SEQ ID NO:15 and CDR-L3 of SEQ ID NO:20;

b) CDR-H1 of SEQ ID NO:25, CDR-H2 of SEQ ID NO:07, CDR-H3 of SEQ ID NO:11 and CDR-L1 of SEQ ID NO:14, CDR-L2 of SEQ ID NO:15 and CDR-L3 of SEQ ID NO:17;

c) CDR-H1 of SEQ ID NO:25, CDR-H2 of SEQ ID NO:08, CDR-H3 of SEQ ID NO:12 and CDR-L1 of SEQ ID NO:14, CDR-L2 of SEQ ID NO:15 and CDR-L3 of SEQ ID NO:18;

d) CDR-H1 of SEQ ID NO:04, CDR-H2 of SEQ ID NO:09, CDR-H3 of SEQ ID NO:13 and CDR-L1 of SEQ ID NO:14, CDR-L2 of SEQ ID NO:15 and CDR-L3 of SEQ ID NO:19;

e) CDR-H1 of SEQ ID NO:05, CDR-H2 of SEQ ID NO:06, CDR-H3 of SEQ ID NO:10 and CDR-L1 of SEQ ID NO:14, CDR-L2 of SEQ ID NO:15 and CDR-L3 of SEQ ID NO:20; and f) CDR-H1 of SEQ ID NO:26, CDR-H2 of SEQ ID NO:27, CDR-H3 of SEQ ID NO: 10 and CDR-L1 of SEQ ID NO:14, CDR-L2 of SEQ ID NO:15 and CDR-L3 of SEQ ID NO:20.

2. The antibody of claim 1, which blocks binding of a Wnt ligand to the Wnt3a binding site of LRP6.

3. The antibody of claim 1, which blocks binding of a Wnt ligand to the non-Wnt3a binding site of LRP6.

4. The antibody of claim 1, wherein the antibody is a monoclonal antibody.

5. The antibody of claim 1, wherein the antibody is a humanized antibody.

6. The antibody of claim 1, wherein the antibody is a single chain antibody.

7. The antibody of claim 1, wherein the antibody is an antibody binding fragment selected from Fab, Fab', F(ab')2, scFv, dsFv, ds-scFv, dimers, single-domain antibodies, minibodies, diabodies, and multimers thereof.

8. The antibody of claim 1, wherein the antibody is a bi-specific antibody.

9. The antibody of claim 1, wherein the antibody is a bi-specific antibody that further binds to FZD receptor.

10. The antibody of claim 1, comprising a non-natural glycosylation pattern.

11. The antibody of claim 1 comprising a cysteine substitution or addition in the constant region or a framework region.

12. An immunoconjugate comprising the antibody of claim 1, and a detectable label or cytotoxic agent.

13. The immunoconjugate of claim 12, comprising a cytotoxic agent selected from maytansinoid, auristatin, dolastatin, tubulysin, cryptophycin, pyrrolobenzodiazepine (PBD) dimer, indolinobenzodiazepine dimer, alpha-amanitin, trichothene, SN-38, duocarmycin, CC1065, calicheamincin, an enediyne antibioatic, taxane, doxorubicin derivatives, anthracycline and stereoisomers, azanofide, isosteres, analogs or derivatives thereof.

14. A nucleic acid molecule encoding the antibody of claim 1.

15. A method of inhibiting Wnt ligand binding to an LRP6 receptor, disrupting a Wnt signaling pathway, inhibiting Wnt-induced transcriptional activity, inhibiting activation of disheveled, promoting preservation of the beta-catenin destruction complex, promoting accumulation of beta-catenin or inhibiting growth of a cell, the method comprising contacting a cell expressing an LRP6 receptor with an antibody of claim 1 or immunoconjugate of claim 12.

16. A method of treating cancer in a subject in need thereof comprising administering to the subject an effective amount of a pharmaceutical composition comprising an antibody or an immunoconjugate of claim 1.

* * * * *